(12) United States Patent
Murphy et al.

(10) Patent No.: US 7,105,348 B2
(45) Date of Patent: *Sep. 12, 2006

(54) METHODS OF MODIFYING EUKARYOTIC CELLS

(75) Inventors: Andrew J. Murphy, Croton-on-Hudson, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 375 days.

This patent is subject to a terminal disclaimer.

(21) Appl. No.: 10/076,840

(22) Filed: Feb. 15, 2002

(65) Prior Publication Data

US 2002/0183275 A1    Dec. 5, 2002

Related U.S. Application Data

(63) Continuation-in-part of application No. 09/784,859, filed on Feb. 16, 2001, now Pat. No. 6,596,541.

(60) Provisional application No. 60/244,665, filed on Oct. 31, 2000.

(51) Int. Cl.
```
C12N 15/87    (2006.01)
C12N 15/00    (2006.01)
C12N 15/85    (2006.01)
C07H 21/02    (2006.01)
C07H 21/04    (2006.01)
```
(52) U.S. Cl. .................. 435/463; 435/440; 435/455; 536/23.1; 536/23.51

(58) Field of Classification Search ............. 435/172.3, 435/320.1, 463, 440, 455; 536/23.1, 23.51
See application file for complete search history.

(56) References Cited

U.S. PATENT DOCUMENTS 5,436,149 A    7/1995    Barnes
5,789,215 A    8/1998    Berns et al.

FOREIGN PATENT DOCUMENTS

WO    WO94/02602    2/1994

OTHER PUBLICATIONS

Moreadith et al., J. Mol. Med., 1997.*
Mullins et al. Journal of Clinical Investigation, 1996.*
Pera et al. Journal of Cell Science 113: 5-10 (2000).*
Hong et al. Analytical Biochem., 291: 142-148 (2001).*
Giraldo et al. Transgenic Res., 10:83-103 (2001).*
*NATURE, vol. 317, 1985, Smithies, O., et al., "Insertion of DNA sequences into the human chromosomal β-globin locus by homologous recombination," pp. 230-234.
*CELL, vol. 51, 1987, Thomas, K.R., and Capecchi, M.R., "Site-Directed Mutagenesis by Gene Targeting in Mouse Embryo-Derived Stem Cells," pp. 503-512.
*Proc. Natl. Acad. Sci. USA, vol. 86, 1989, Koller, B.H., et al., "Germ-line transmission of a planned alteration made in a hypoxanthine phosphoribosyltransferase gene by homologous recombination in embryonic stem cells," pp. 8927-8931.
*SCIENCE, vol. 254, 1991, Kuhn, R., et al., "Generation and Analysis of Interleukin-4 Deficient Mice," pp. 707-710.
*NATURE, vol. 346, 1990, Thomas, K.R., and Capecchi, M.R., "Targeted disruption of the murine int-1 proto-oncogene resulting in severe abnormalities in midbrain and cerebellar development," pp. 847-850.
*SCIENCE, vol. 246, 1989, Scwartzberg, P.L., et al., "Germ-line Transmission of c-abl Mutation produced by Targeted Gene Disruption in ES Cells," pp. 799-803.
*NATURE, vol. 330, 1987, Doetschman, T., et al., "Targetted correction of a mutant HPRT gene in mouse embryonic stem cells," pp. 576-578.
*CELL, vol. 56, 1989, Thompson, S., et al., "Germ Line Transmission and Expression of a Corrected HPRT Gene Produced by Gene Targeting in Embryonic stem Cells," pp. 313-321.
*NATURE, vol. 345, 1990, DeChiara, T.M., et al., "A growth-deficiency phenotype in heterozygous mice carrying an insulin-like growth factor II gene disrupted by targeting," pp. 78-80.
*NATURE, vol. 369, 1994, Cheng, S., et al., "Long PCR," pp. 684-685.
*PCR Methods and Applications, 1994, Foord, O.S., and Rose, E.A., "Long-distance PCR," pp. 3:S149-S161.
*Nucleic Acids Research, vol. 20 No. 3, 1992, Ponce, M.R., and Micol, J.L., "PCR amplification of long DNA fragments," p. 623.
*Gene Targeting-A Practical Approach, 2nd Ed., 2000, Edited by Joyner, A.L., Hasty, P. et al., Chapter 1 "Gene targeting, principles, and practice in mammalian cells," pp. 1-35.
*Molecular and Cellular Biology, vol. 12 No. 8, 1992, Deng, C., and Capecchi, M.R., "Reexamination of Gene Targeting Frequency as a Function of the Extent of Homology between the Targeting Vector and the Target Locus," pp. 3365-3371.

(Continued)

Primary Examiner—Anne-Marie Falk
Assistant Examiner—Thaian N. Ton
(74) Attorney, Agent, or Firm—Valeta Gregg, Esq.

(57) ABSTRACT

A method for engineering and utilizing large DNA vectors to target, via homologous recombination, and modify, in any desirable fashion, endogenous genes and chromosomal loci in eukaryotic cells. These large DNA targeting vectors for eukaryotic cells, termed LTVECs, are derived from fragments of cloned genomic DNA larger than those typically used by other approaches intended to perform homologous targeting in eukaryotic cells. Also provided is a rapid and convenient method of detecting eukaryotic cells in which the LTVEC has correctly targeted and modified the desired endogenous gene(s) or chromosomal locus (loci) as well as the use of these cells to generate organisms bearing the genetic modification.

15 Claims, 7 Drawing Sheets

OTHER PUBLICATIONS

*Nature Genetics, vol. 20, 1998, Zhang, Y., et al., "A new logic for DNA engineering using recombination in *Escherichia coli*," pp. 123-128.
*Nucleic Acids Research, vol. 27, 1999, Angrand, P., et al, "Simplified generation of targeting constructs using ET recombination," pp. 16(e).
*Nucleic Acids Research, vol. 27, 1999, Muyrers, J.P., et al., "Rapid modification of bacterial artificial chromosomes by ET-recombination," pp. 1555-1557.
*Gene Therapy, vol. 6, 1999, Narayanan, K. et al., "Efficient and precise engineering of a 200kb β-globin human/bacterial artificial chromosome in *E. coli* DH10B using an inducible homologous recombination system," pp. 442-447.
*GENOMICS, vol. 64, 1999, Hill, F., et al., "BAC Trimming: Minimizing Clone Overlaps," pp. 111-113.
*Nature Biotechnology, vol. 15, 1997, Yang, X, et al., "Homologous recombination based modification in *Escherichia coli* and germline transmission in transgenic mice of a bacterial artificial chromosome," pp. 859-865.
*Proc. Natl. Acad. Sci. USA, vol. 97, 2000, Yu, D., et al., "An efficient recombination system for chromosome engineering in *Escherichia coli*," pp. 5978-5983.
*Proc. Natl. Acad. Sci. USA, vol. 91, 1994, Hall, S. D, and Kolodner, R.D.,"Homologous pairing and strand exchange promoted by the *Escherichia coli* RecT protein," pp. 3205-3209.
*GENE, vol. 138, 1994, Kusano, K., et al., "Involvement of RecE and RectT annealing protein in DNA double-stranded break repair by homologous recombination," pp. 17-25.
*Science, vol. 277, 1997, Kovall, R, and Matthews, B.W., "Toroidal Structure of λ-Exonuclease," pp. 1824-1827.
*Cold Springs Harb Symp Quant Biol, vol. 49, 1984, Clark, A.J., et al., "Genes of the RecE and RecF Pathways of Conjugational Recombination in *Escherichia coli*," pp. 453-462.
*J Biol Chem, vol. 273, 1998, Noirot, P., and Kolodner, R.D., "DNA Stand Invasion Promoted by *Escherichia coli* RecT Protein," pp. 12274-12280.
*J Mol Biol, vol. 254, 1995, Thresher, et al., "Electron Microscopic Visualization of RecT Protein and its Complexes with DNA," pp. 364-371.
*Molecular Microbiology, vol. 11, 1994, Kolodner, et al., "Homologous pairing proteins encoded by the *Escherichia coli recE* and *recT* genes," p. 23-30.
*Journal of Bacteriology, vol. 175, 1993, Hall, S.D., et al., "Identification and Characterization of the *Escherichia coli* RecT Protein, a Protein Encoded by the *recE* Region That Promotes Renaturation of Homologous Single-Stranded DNA," pp. 277-287.
*Journal of Bacteriology, vol. 173, 1991, Murphy, K.C., "λ Gam Protein Inhibits the Helicase and χ-Stimulated Recombination Activities of *Escherichia coli* RecBCD Enzyme," pp. 5808-5821.
*Journal of Bacteriology, vol. 170, 1988, Poteete, A.R., and Fenton, A.C., "Modulation of *Escherichia coli* RecBCD Activity by the Bacteriophage λ Gam and P22 Abc Functions," pp. 2012-2021.
*Annu Rev Genet, vol. 28, 1994, Myers, R.S., and Stahl, F.W., "χ and the RecBC D Enzymen of *Escherichia coli*," pp. 49-70.
*The Journal of Biological Chemistry, vol. 259. 1984, Abremski K., and Hoess, R., "Bacteriophage P1 Site-specific Recombination-Purification and Properties of the Cre Recombinase Protein," pp. 1509-1514.
*Cell, vol. 40, 1985, Andrews, B.J., et al., "The FLP Recombinase of the 2μ Circle DNA of Yeast: Interaction with Its Target Sequences," p. 795-803.
*Cold Spring Harb Symp Quant Biol, vol. 49, Meyer-Leon, L., et al., "Site-specific Genetic Recombination Promoted by the FLP Protein of the Yeast 2-micron Plasmid In Vitro," pp. 797-804.
*Proc Natl Acad Sci USA, vol. 80, 1983, Cox, M.M., "The FLP protein of the yeast 2-μm plasmid: Expression of a eukaryotic genetic recombination system in *Escherichia coli*," pp. 4223-4227.
*Curr Opin Biotechnol, vol. 9, 1998, Lie, Y.S., and Petropoulos, C.J., "Advances in quantitative PCR technology: 5' nuclease assays," pp. 43-48.

*Eur J Chem, vol. 6, 2000, Tan, W., et al., "Molecular Beacons: A Novel DNA Probe for Nucleic Acid and Protein," pp. 1107-1111.
*Hum Genet, vol. 96, 1995, Laan, M., et al., "Solid-phase minisequencing confirmed by FISH analysis in determination of gene copy number," pp. 275-280.
*Trends in Genetics, vol. 13, 1997, Forozan, F., et al., "Genome screening by comparative genomic hybridization," pp. 405-409.
*Journal of Cellular Biochemistry, vol. 17G, 1993, Thompson, C.T., and Gray, J.W., "Cytogenetic Profiling Using Fluorescence *In Situ* Hybridization (FISH) and Comparative Genomic Hybridization (CGH)," pp. 139-143.
*American Journal of Pathology, vol. 145, 1994, Houldsworth, J, and Chaganti, R.S.K., "Comparative Genomic Hybridization: An Overview," p. 1253-1260.
*Nature Genetics, vol. 19, 1998, Lizardi, P.M., et al., "Mutation detection and single-molecule counting using isothermal rolling-circle amplification," pp. 225-232.
*Nucleic Acids Research, vol. 27, 1999, Mitra, R.D., and Church, G.M., "*In situ* localized amplification and contact replication of many individual DNA molecules," pp. e34.
Nucleic Acids Research, vol. 25, No. 14, 1997, Bethke, Bruce And Sauer, Brian, "Segmental genomic replacement by Cre-Mediated recombination: genotoxic stress activation of the p53 promoter in single-copy transformants", pp. 2828-2834.
Molecular Immunology, vol. 33, No. 17/18, 1996, Shigeharu Fujieda, et al., "Direct Evidence That γ1 And γ3 Switching In Human B Cells Is Interleukin-10 Dependent", pp. 1335-1343.
Eur. J. Immunol., vol. 28, 1998, Brain B. Haines and Peter H. Brodeur, "Accessibility changes across the mouse Igh-V locus during B cell development", pp. 4228-4235.
Nature Genetics, vol. 20, 1998, Herault, Yann, et al., "Engineering chromosomes in mice through targeted meiotic recombination (TAMERE)", pp. 381-384.
Nucleic Acids Research, vol. 14, No. 5, 1986, Hoess, Ronald H., et al., "The role of the *loxP* spacer region in PI site-specific recombination", pp. 2287-2300.
Eur. J. Immunol, vol. 6, 1976, G. Kohler and C Milstein, "Derivation of specific antibody-producing tissue culture and tumor lines by cell fusion", pp. 511-519.
Analytical Biochemistry, vol. 290, 2001, Andreas F. Kolb, "Selection-Marker-Free Modification of the Murine β-Casein Gene Using a *lox*2722 Site", pp. 260-271.
Current Opinion in Biotechnology, vol. 9, 1998, Yolanda S. Lie and Christos J. Petropoulos, "Advances in quantitative PCR technology: 5' nuclease assays", pp. 43-48.
The Journal of Immunology, 1998, Ong, Jane, et al., "3' IgH Enhancer Elements Shift Synergistic Interactions During B Cell Development", pp. 4896-4903.
Eur. J. Immunol., vol, 30, 2000, Pan, Qiang,et al., "Regulation of the promoter for human immunoglobulin γ3 germ-line transcription and its interaction with the 3'α enhancer", pp. 1019-1029.
Molecular and Cellular Biology, vol. 19, No. 10, Oct. 1999, Ronai, Diana, et al., "Variegated Expression of the Endogenous Immunoglobulin Heavy-Chain Gene in the Absence of the Intronic Locus Control Region", pp. 7031-7040.
PNAS, vol. 97, No. 2, Jan. 18, 2000, Tomizuka, Kazuma, et al., "Double trans-chromosomic mice: Maintenance of two individual human chromosome fragments containing Ig heavy and κ loci and expression of ully human antibodies", pp. 722-727.
Faculty of Biology, University of Konstanz, Germany, 1999, Willers, Jörg, et al., "Apparent Trans-Chromosomal Antibody Class Switch in Mice Bearing an $Igh^\alpha$ μ-chain Transgene on an $Igh^b$ Genetic Background", pp. 150-164.
Nature Biotechnology, vol. 15, Sep. 1997, Yang, Xiangdong W. , et al., "Homologous recombination based modification in *Esherichia coli* and germline transmission in transgenic mice of a bacterial artificial chromosome", (sic) pp. 859-865.
Jessen, et al., Proc. Natl. Acad. Sci. USA, vol. 95, pp. 5121-5126, (1998).

* cited by examiner

FIGURE 3A

```
           10         20         30         40         50         60
   CCCCGGGCTT CCTGTTCTAA TAAGAATACC TCCTAGGTCC CCCATGGGCT AACCTCATCT
   GGGGCCCGAA GGACAAGATT ATTCTTATGG AGGATCCAGG GGGTACCCGA TTGGAGTAGA 70         80         90        100        110        120
   TTGGTACTCA ACAGGGGTCT TCTTTATGAG CTTCGGACCA GCTCTTTTGA TGTGGCAGGG
   AACCATGAGT TGTCCCCAGA AGAAATACTC GAAGCCTGGT CGAGAAAACT ACACCGTCCC 130        140        150        160        170        180
   ACTGACCCTG GGTGGGGAAG CCACTCAGTG CATGACCCCA GCTGGTTCAC CACATATACC
   TGACTGGGAC CCACCCCTTC GGTGAGTCAC GTACTGGGGT CGACCAAGTG GTGTATATGG 190        200        210        220            230
   ACATACTTTT CTTGCAGGTC TGGGACACAG C ATG CCC CGG GGC CCA GTG GCT GCC
   TGTATGAAAA GAACGTCCAG ACCCTGTGTC G TAC GGG GCC CCG GGT CAC CGA CGG
                                      Met Pro Arg Gly Pro Val Ala Ala>

240        250        260        270        280
   TTA CTC CTG CTG ATT CTC CAT GGA GCT TGG AGC TGC CTG GAC CTC ACT
   AAT GAG GAC GAC TAA GAG GTA CCT CGA ACC TCG ACG GAC CTG GAG TGA
   Leu Leu Leu Leu Ile Leu His Gly Ala Trp Ser Cys Leu Asp Leu Thr>

290        300        310        320        330
   TGC TAC ACT GAC TAC CTC TGG ACC ATC ACC TGT GTC CTG GAG ACA CGG
   ACG ATG TGA CTG ATG GAG ACC TGG TAG TGG ACA CAG GAC CTC TGT GCC
   Cys Tyr Thr Asp Tyr Leu Trp Thr Ile Thr Cys Val Leu Glu Thr Arg>

340        350        360        370
   AGC CCC AAC CCC AGC ATA CTC AGT CTC ACC TGG CAA GAT GAA TAT GAG
   TCG GGG TTG GGG TCG TAT GAG TCA GAG TGG ACC GTT CTA CTT ATA CTC
   Ser Pro Asn Pro Ser Ile Leu Ser Leu Thr Trp Gln Asp Glu Tyr Glu>

380         390        400        410        420
   GAA CTT CAG GAC CAA GAG ACC TTC TGC AGC CTA CAC AAG TCT GGC CAC
   CTT GAA GTC CTG GTT CTC TGG AAG ACG TCG GAT GTG TTC AGA CCG GTG
   Glu Leu Gln Asp Gln Glu Thr Phe Cys Ser Leu His Lys Ser Gly His>

430        440        450        460        470
   AAC ACC ACA CAT ATA TGG TAC ACG TGC CAT ATG CGC TTG TCT CAA TTC
   TTG TGG TGT GTA TAT ACC ATG TGC ACG GTA TAC GCG AAC AGA GTT AAG
   Asn Thr Thr His Ile Trp Tyr Thr Cys His Met Arg Leu Ser Gln Phe>

480        490        500        510        520
   CTG TCC GAT GAA GTT TTC ATT GTC AAC GTG ACG GAC CAG TCT GGC AAC
   GAC AGG CTA CTT CAA AAG TAA CAG TTG CAC TGC CTG GTC AGA CCG TTG
   Leu Ser Asp Glu Val Phe Ile Val Asn Val Thr Asp Gln Ser Gly Asn>

530        540        550        560        570
   AAC TCC CAA GAG TGT GGC AGC TTT GTC CTG GCT GAG AGC ATC AAG CCA
   TTG AGG GTT CTC ACA CCG TCG AAA CAG GAC CGA CTC TCG TAG TTC GGT
   Asn Ser Gln Glu Cys Gly Ser Phe Val Leu Ala Glu Ser Ile Lys Pro>
```

FIGURE 3B

```
          580             590             600             610
 GCT CCC CCC TTG AAC GTG ACT GTG GCC TTC TCA GGA CGC TAT GAT ATC
 CGA GGG GGG AAC TTG CAC TGA CAC CGG AAG AGT CCT GCG ATA CTA TAG
 Ala Pro Pro Leu Asn Val Thr Val Ala Phe Ser Gly Arg Tyr Asp Ile>

620             630             640             650             660
 TCC TGG GAC TCA GCT TAT GAC GAA CCC TCC AAC TAC GTG CTG AGA GGC
 AGG ACC CTG AGT CGA ATA CTG CTT GGG AGG TTG ATG CAC GAC TCT CCG
 Ser Trp Asp Ser Ala Tyr Asp Glu Pro Ser Asn Tyr Val Leu Arg Gly>

670             680             690             700             710
 AAG CTA CAA TAT GAG CTG CAG TAT CGG AAC CTC AGA GAC CCC TAT GCT
 TTC GAT GTT ATA CTC GAC GTC ATA GCC TTG GAG TCT CTG GGG ATA CGA
 Lys Leu Gln Tyr Glu Leu Gln Tyr Arg Asn Leu Arg Asp Pro Tyr Ala>

720             730             740             750             760
 GTG AGG CCG GTG ACC AAG CTG ATC TCA GTG GAC TCA AGA AAC GTC TCT
 CAC TCC GGC CAC TGG TTC GAC TAG AGT CAC CTG AGT TCT TTG CAG AGA
 Val Arg Pro Val Thr Lys Leu Ile Ser Val Asp Ser Arg Asn Val Ser>

770             780             790             800             810
 CTT CTC CCT GAA GAG TTC CAC AAA GAT TCT AGC TAC CAG CTG CAG ATG
 GAA GAG GGA CTT CTC AAG GTG TTT CTA AGA TCG ATG GTC GAC GTC TAC
 Leu Leu Pro Glu Glu Phe His Lys Asp Ser Ser Tyr Gln Leu Gln Met>

820             830             840             850
 CGG GCA GCG CCT CAG CCA GGC ACT TCA TTC AGG GGG ACC TGG AGT GAG
 GCC CGT CGC GGA GTC GGT CCG TGA AGT AAG TCC CCC TGG ACC TCA CTC
 Arg Ala Ala Pro Gln Pro Gly Thr Ser Phe Arg Gly Thr Trp Ser Glu>

860             870             880             890             900
 TGG AGT GAC CCC GTC ATC TTT CAG ACC CAG GCT GGG GAG CCC GAG GCA
 ACC TCA CTG GGG CAG TAG AAA GTC TGG GTC CGA CCC CTC GGG CTC CGT
 Trp Ser Asp Pro Val Ile Phe Gln Thr Gln Ala Gly Glu Pro Glu Ala>

910             920             930             940             950
 GGC TGG GAC CCT CAC ATG CTG CTG CTC CTG GCT GTC TTG ATC ATT GTC
 CCG ACC CTG GGA GTG TAC GAC GAC GAG GAC CGA CAG AAC TAG TAA CAG
 Gly Trp Asp Pro His Met Leu Leu Leu Leu Ala Val Leu Ile Ile Val>

960             970             980             990             1000
 CTG GTT TTC ATG GGT CTG AAG ATC CAC CTG CCT TGG AGG CTA TGG AAA
 GAC CAA AAG TAC CCA GAC TTC TAG GTG GAC GGA ACC TCC GAT ACC TTT
 Leu Val Phe Met Gly Leu Lys Ile His Leu Pro Trp Arg Leu Trp Lys>

1010            1020            1030            1040            1050
 AAG ATA TGG GCA CCA GTG CCC ACC CCT GAG AGT TTC TTC CAG CCC CTG
 TTC TAT ACC CGT GGT CAC GGG TGG GGA CTC TCA AAG AAG GTC GGG GAC
 Lys Ile Trp Ala Pro Val Pro Thr Pro Glu Ser Phe Phe Gln Pro Leu>
```

FIGURE 3C

```
           1060           1070           1080           1090
  TAC AGG GAG CAC AGC GGG AAC TTC AAG AAA TGG GTT AAT ACC CCT TTC
  ATG TCC CTC GTG TCG CCC TTG AAG TTC TTT ACC CAA TTA TGG GGA AAG
  Tyr Arg Glu His Ser Gly Asn Phe Lys Lys Trp Val Asn Thr Pro Phe>

1100           1110           1120           1130           1140
  ACG GCC TCC AGC ATA GAG TTG GTG CCA CAG AGT TCC ACA ACA ACA TCA
  TGC CGG AGG TCG TAT CTC AAC CAC GGT GTC TCA AGG TGT TGT TGT AGT
  Thr Ala Ser Ser Ile Glu Leu Val Pro Gln Ser Ser Thr Thr Thr Ser>

1150           1160           1170           1180           1190
  GCC TTA CAT CTG TCA TTG TAT CCA GCC AAG GAG AAG AAG TTC CCG GGG
  CGG AAT GTA GAC AGT AAC ATA GGT CGG TTC CTC TTC TTC AAG GGC CCC
  Ala Leu His Leu Ser Leu Tyr Pro Ala Lys Glu Lys Lys Phe Pro Gly>

1200           1210           1220           1230           1240
  CTG CCG GGT CTG GAA GAG CAA CTG GAG TGT GAT GGA ATG TCT GAG CCT
  GAC GGC CCA GAC CTT CTC GTT GAC CTC ACA CTA CCT TAC AGA CTC GGA
  Leu Pro Gly Leu Glu Glu Gln Leu Glu Cys Asp Gly Met Ser Glu Pro>

1250           1260           1270           1280           1290
  GGT CAC TGG TGC ATA ATC CCC TTG GCA GCT GGC CAA GCG GTC TCA GCC
  CCA GTG ACC ACG TAT TAG GGG AAC CGT CGA CCG GTT CGC CAG AGT CGG
  Gly His Trp Cys Ile Ile Pro Leu Ala Ala Gly Gln Ala Val Ser Ala>

1300           1310           1320           1330
  TAC AGT GAG GAG AGA GAC CGG CCA TAT GGT CTG GTG TCC ATT GAC ACA
  ATG TCA CTC CTC TCT CTG GCC GGT ATA CCA GAC CAC AGG TAA CTG TGT
  Tyr Ser Glu Glu Arg Asp Arg Pro Tyr Gly Leu Val Ser Ile Asp Thr>

1340           1350           1360           1370           1380
  GTG ACT GTG GGA GAT GCA GAG GGC CTG TGT GTC TGG CCC TGT AGC TGT
  CAC TGA CAC CCT CTA CGT CTC CCG GAC ACA CAG ACC GGG ACA TCG ACA
  Val Thr Val Gly Asp Ala Glu Gly Leu Cys Val Trp Pro Cys Ser Cys>

1390           1400           1410           1420           1430
  GAG GAT GAT GGC TAT CCA GCC ATG AAC CTG GAT GCT GGC AGA GAG TCT
  CTC CTA CTA CCG ATA GGT CGG TAC TTG GAC CTA CGA CCG TCT CTC AGA
  Glu Asp Asp Gly Tyr Pro Ala Met Asn Leu Asp Ala Gly Arg Glu Ser>

1440           1450           1460           1470           1480
  GGT CCT AAT TCA GAG GAT CTG CTC TTG GTC ACA GAC CCT GCT TTT CTG
  CCA GGA TTA AGT CTC CTA GAC GAG AAC CAG TGT CTG GGA CGA AAA GAC
  Gly Pro Asn Ser Glu Asp Leu Leu Leu Val Thr Asp Pro Ala Phe Leu>

1490           1500           1510           1520           1530
  TCT TGT GGC TGT GTC TCA GGT AGT GGT CTC AGG CTT GGG GGC TCC CCA
  AGA ACA CCG ACA CAG AGT CCA TCA CCA GAG TCC GAA CCC CCG AGG GGT
  Ser Cys Gly Cys Val Ser Gly Ser Gly Leu Arg Leu Gly Gly Ser Pro>
```

Figure 3D

```
          1540            1550            1560            1570
   GGC AGC CTA CTG GAC AGG TTG AGG CTG TCA TTT GCA AAG GAA GGG GAC
   CCG TCG GAT GAC CTG TCC AAC TCC GAC AGT AAA CGT TTC CTT CCC CTG
   Gly Ser Leu Leu Asp Arg Leu Arg Leu Ser Phe Ala Lys Glu Gly Asp>

1580            1590            1600            1610            1620
    TGG ACA GCA GAC CCA ACC TGG AGA ACT GGG TCC CCA GGA GGG GGC TCT
    ACC TGT CGT CTG GGT TGG ACC TCT TGA CCC AGG GGT CCT CCC CCG AGA
    Trp Thr Ala Asp Pro Thr Trp Arg Thr Gly Ser Pro Gly Gly Gly Ser>

1630            1640            1650            1660            1670
    GAG AGT GAA GCA GGT TCC CCC CCT GGT CTG GAC ATG GAC ACA TTT GAC
    CTC TCA CTT CGT CCA AGG GGG GGA CCA GAC CTG TAC CTG TGT AAA CTG
    Glu Ser Glu Ala Gly Ser Pro Pro Gly Leu Asp Met Asp Thr Phe Asp>

1680            1690            1700            1710            1720
    AGT GGC TTT GCA GGT TCA GAC TGT GGC AGC CCC GTG GAG ACT GAT GAA
    TCA CCG AAA CGT CCA AGT CTG ACA CCG TCG GGG CAC CTC TGA CTA CTT
    Ser Gly Phe Ala Gly Ser Asp Cys Gly Ser Pro Val Glu Thr Asp Glu>

1730            1740            1750            1760            1770
    GGA CCC CCT CGA AGC TAT CTC CGC CAG TGG GTG GTC AGG ACC CCT CCA
    CCT GGG GGA GCT TCG ATA GAG GCG GTC ACC CAC CAG TCC TGG GGA GGT
    Gly Pro Pro Arg Ser Tyr Leu Arg Gln Trp Val Val Arg Thr Pro Pro>

1780            1790            1800
    CCT GTG GAC AGT GGA GCC CAG AGC AGC TAG
    GGA CAC CTG TCA CCT CGG GTC TCG TCG ATC
    Pro Val Asp Ser Gly Ala Gln Ser Ser ***>
```

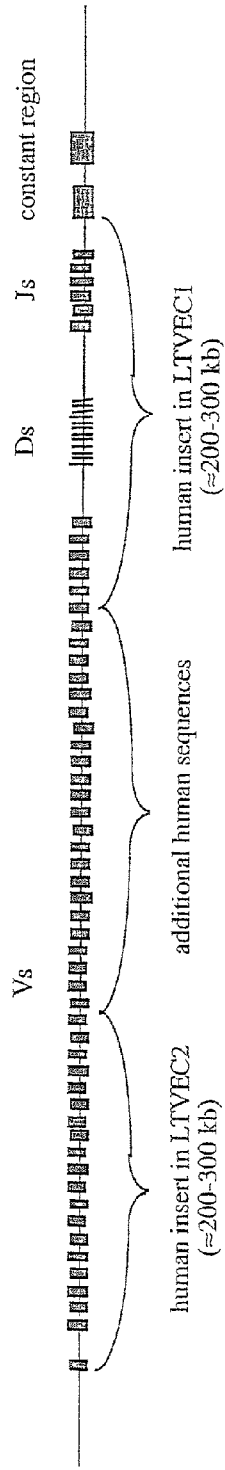
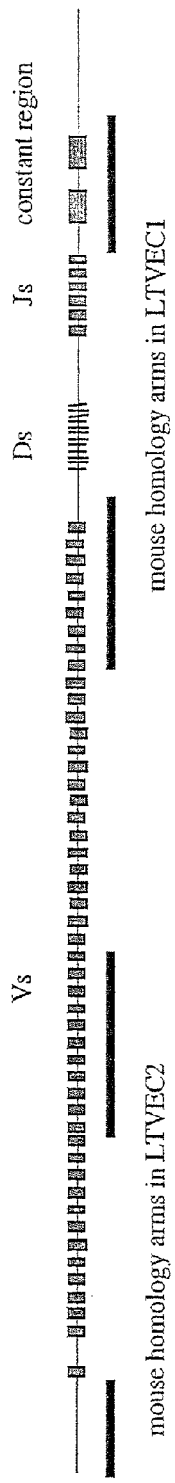
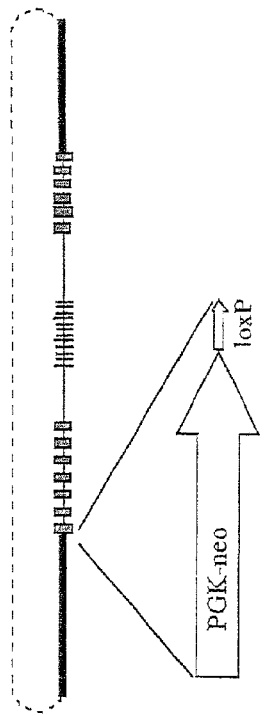
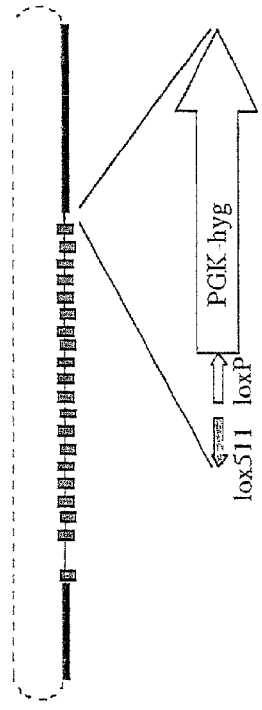
Figure 4A Human Ig heavy chain locus (total length ≈1Mb, not drawn to scale):
human insert in LTVEC2 (≈200-300 kb)
additional human sequences
human insert in LTVEC1 (≈200-300 kb)
Figure 4B Mouse IG heavy chain locus (total length ≈1Mb, not drawn to scale):
mouse homology arms in LTVEC2
mouse homology arms in LTVEC1
Figure 4C LTVEC2:
Figure 4d LTVEC1:

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Mouse OCR10 gene primer

<400> SEQUENCE: 1
agctaccagc tgcagatgcg ggcag                                    25

<210> SEQ ID NO 2
<211> LENGTH: 28
<212> TYPE: DNA
<213> ORGANISM: Artificial Sequence
<220> FEATURE:
<223> OTHER INFORMATION: Mouse OCR10 gene primer

<400> SEQUENCE: 2
ctccccagcc tgggtctgaa agatgacg                                 28

<210> SEQ ID NO 3
<211> LENGTH: 24
<212> TYPE: DNA
<213> ORGANISM: Artificial Sequence
<220> FEATURE:
<223> OTHER INFORMATION: Mouse OCR10 gene primer

<400> SEQUENCE: 3
gacctcactt gctacactga ctac                                     24

<210> SEQ ID NO 4
<211> LENGTH: 28
<212> TYPE: DNA
<213> ORGANISM: Artificial Sequence
<220> FEATURE:
<223> OTHER INFORMATION: Mouse OCR10 gene primer

<400> SEQUENCE: 4
acttgtgtag gctgcagaag gtctcttg                                 28

<210> SEQ ID NO 5
<211> LENGTH: 1799
<212> TYPE: DNA
<213> ORGANISM: Artificial Sequence
<220> FEATURE:
<223> OTHER INFORMATION: Mouse OCR10 cDNA

<400> SEQUENCE: 5
ccccgggctt cctgttctaa taagaatacc tcctaggtcc cccatgggct aacctcatct      60
ttggtactca acagggtct tctttatgag cttcggacca gctcttttga tgtggcaggg      120
actgaccctg ggtggggaag ccactcagtg catgacccca gctggttcac cacatatacc     180
acatactttt cttgcaggtc tgggacacag catgccccgg ggcccagtgg ctgccttact     240
cctgctgatt ctccatggag cttggagctg cctggacctc acttgctaca ctgactacct     300
ctggaccatc acctgtgtcc tggagacacg gagcccaaac cccagcatac tcagtctcac     360
ctggcaagat gaatatgagg aacttcagga ccaagagacc ttctgcagcc tacacaagtc     420
tggccacaac accacacata tatggtacac gtgccatatg cgcttgtctc aattcctgtc     480
cgatgaagtt ttcattgtca acgtgacgga ccagtctggc aacaactccc aagagtgtgg     540

-continued

```
cagctttgtc ctggctgaga gcatcaagcc agctccccccc ttgaacgtga ctgtggcctt      600
ctcaggacgc tatgatatct cctgggactc agcttatgac gaaccctcca actacgtgct      660
gagaggcaag ctacaatatg agctgcagta cggaacctc agagacccct atgctgtgag       720
gccggtgacc aagctgatct cagtggactc aagaaacgtc tctcctccct gaagagttcc      780
acaaagattc tagctaccag ctgcagatgc gggcagcgcc tcagccaggc acttcattca      840
ggggggacctg gagtgagtgg agtgaccccg tcatctttca gacccaggct ggggagcccg     900
aggcaggctg ggaccctcac atgctgctgc tcctggctgt cttgatcatt gtcctggttt      960
tcatgggtct gaagatccac ctgccttgga ggctatgaa aaagatatgg gcaccagtgc      1020
ccacccctga gagtttcttc cagcccctgt acagggagca cagcgggaac ttcaagaaat     1080
gggttaatac ccctttcacg gcctccagca tagagttggt gccacagagt tccacaacaa     1140
catcagcctt acatctgtca ttgtatccag ccaaggagaa gaagttcccg gggctgccgg     1200
gtctggaaga gcaactggag tgtgatggaa tgtctgagcc tggtcactgg tgcataatcc     1260
ccttggcagc tggccaagcg gtctcagcct acagtgagga gagagaccgg ccatatggtc     1320
tggtgtccat tgacacagtg actgtgggag atgcagaggg cctgtgtgtc tggccctgta     1380
gctgtgagga tgatggctat ccagccatga acctggatgc tggcagagag tctggtccta     1440
attcagagga tctgctcttg gtcacagacc ctgcttttct gtcttgtggc tgtgtctcag     1500
gtagtggtct caggcttggg ggctccccag gcagcctact ggacaggttg aggctgtcat     1560
ttgcaaagga agggactgg acagcagacc caacctggaa actgggtcc ccaggagggg      1620
gctctgagag tgaagcaggt tccccccctg gtctggacat ggacacattt gacagtggct     1680
ttgcaggttc agactgtggc agcccgtgg agactgatga aggaccccct cgaagctatc      1740
tccgccagtg ggtggtcagg acccctccac ctgtggacag tggagcccag agcagctag      1799
```

<210> SEQ ID NO 6
<211> LENGTH: 529
<212> TYPE: PRT
<213> ORGANISM: Artificial Sequence
<220> FEATURE:
<223> OTHER INFORMATION: Mouse OCR10 protein

<400> SEQUENCE: 6

```
Met Pro Arg Gly Pro Val Ala Ala Leu Leu Leu Ile Leu His Gly
 1               5                  10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
            35                  40                  45

Leu Thr Trp Gln Asp Glu Tyr Glu Glu Leu Gln Asp Gln Glu Thr Phe
        50                  55                  60

Cys Ser Leu His Lys Ser Gly His Asn Thr Thr His Ile Trp Tyr Thr
    65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140
```

```
Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Met Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
                260                 265                 270

Pro Glu Ser Phe Phe Gln Pro Leu Tyr Arg Glu His Ser Gly Asn Phe
            275                 280                 285

Lys Lys Trp Val Asn Thr Pro Phe Thr Ala Ser Ser Ile Glu Leu Val
        290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335

Glu Cys Asp Gly Met Ser Glu Pro Gly His Trp Cys Ile Ile Pro Leu
                340                 345                 350

Ala Ala Gly Gln Ala Val Ser Ala Tyr Ser Glu Glu Arg Asp Arg Pro
            355                 360                 365

Tyr Gly Leu Val Ser Ile Asp Thr Val Thr Val Gly Asp Ala Glu Gly
        370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
                420                 425                 430

Gly Leu Arg Leu Gly Gly Ser Pro Gly Ser Leu Leu Asp Arg Leu Arg
            435                 440                 445

Leu Ser Phe Ala Lys Glu Gly Asp Trp Thr Ala Asp Pro Thr Trp Arg
    450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Pro Val Asp Ser Gly Ala Gln Ser
        515                 520                 525

Ser
```

METHODS OF MODIFYING EUKARYOTIC CELLS

This application is a continuation-in-part of U.S. patent application Ser. No. 09/784,859, filed Feb. 16, 2001, issued as U.S. Pat. No. 6,596,541 on Jul. 22, 2003, which claims priority to U.S. patent application Ser. No. 09/732,234 filed Dec. 7, 2000, issued as U.S. Pat. No. 6,586,251 Jul. 1, 2003, which claims priority to U.S. patent application Ser. No. 60/244,665 filed Oct. 31, 2000, which is incorporated by reference herein. Throughout this application various publications are referenced. The disclosures of these publications in their entireties are hereby incorporated by reference into this application.

FIELD OF THE INVENTION

The field of this invention is a method for engineering and utilizing large DNA vectors to target, via homologous recombination, and modify, in any desirable fashion, endogenous genes and chromosomal loci in eukaryotic cells. These large DNA targeting vectors for eukaryotic cells, termed LTVECs, are derived from fragments of cloned genomic DNA larger than those typically used by other approaches intended to perform homologous targeting in eukaryotic cells. The field of the invention further provides for a rapid and convenient method of detecting eukaryotic cells in which the LTVEC has correctly targeted and modified the desired endogenous gene(s) or chromosomal locus (loci). The field also encompasses the use of these cells to generate organisms bearing the genetic modification, the organisms, themselves, and methods of use thereof.

INTRODUCTION

The use of LTVECs provides substantial advantages over current methods. For example, since these are derived from DNA fragments larger than those currently used to generate targeting vectors, LTVECs can be more rapidly and conveniently generated from available libraries of large genomic DNA fragments (such as BAC and PAC libraries) than targeting vectors made using current technologies. In addition, larger modifications as well as modifications spanning larger genomic regions can be more conveniently generated than using current technologies. Furthermore, the present invention takes advantage of long regions of homology to increase the targeting frequency of "hard to target" loci, and also diminishes the benefit, if any, of using isogenic DNA in these targeting vectors.

The present invention thus provides for a rapid, convenient, and streamlined method for systematically modifying virtually all the endogenous genes and chromosomal loci of a given organism.

BACKGROUND OF THE INVENTION

Gene targeting by means of homologous recombination between homologous exogenous DNA and endogenous chromosomal sequences has proven to be an extremely valuable way to create deletions, insertions, design mutations, correct gene mutations, introduce transgenes, or make other genetic modifications in mice. Current methods involve using standard targeting vectors, with regions of homology to endogenous DNA typically totaling less than 10–20 kb, to introduce the desired genetic modification into mouse embryonic stem (ES) cells, followed by the injection of the altered ES cells into mouse embryos to transmit these engineered genetic modifications into the mouse germline (Smithies et al., Nature, 317:230–234, 1985; Thomas et al., Cell, 51:503–512, 1987; Koller et al., Proc Natl Acad Sci USA, 86:8927–8931, 1989; Kuhn et al., Science, 254: 707–710, 1991; Thomas et al., Nature, 346:847–850, 1990; Schwartzberg et al., Science, 246:799–803, 1989; Doetschman et al., Nature, 330:576–578, 1987; Thomson et al., Cell, 5:313–321, 1989; DeChiara et al., Nature, 345:78–80, 1990; U.S. Pat. No. 5,789,215, issued Aug. 4, 1998 in the name of GenPharm International) In these current methods, detecting the rare ES cells in which the standard targeting vectors have correctly targeted and modified the desired endogenous gene(s) or chromosomal locus(loci) requires sequence information outside of the homologous targeting sequences contained within the targeting vector. Assays for successful targeting involve standard Southern blotting or long PCR (Cheng, et al., Nature, 369:684–5, 1994; Foord and Rose, PCR Methods Appl, 3:S149–61, 1994; Ponce and Micol, Nucleic Acids Res, 20:623, 1992; U.S. Pat. No. 5,436,149 issued to Takara Shuzo Co., Ltd.) from sequences outside the targeting vector and spanning an entire homology arm (see Definitions); thus, because of size considerations that limit these methods, the size of the homology arms are restricted to less than 10–20 kb in total (Joyner, The Practical Approach Series, 293, 1999).

The ability to utilize targeting vectors with homology arms larger than those used in current methods would be extremely valuable. For example, such targeting vectors could be more rapidly and conveniently generated from available libraries containing large genomic inserts (e.g. BAC or PAC libraries) than targeting vectors made using current technologies, in which such genomic inserts have to be extensively characterized and trimmed prior to use. In addition, larger modifications as well as modifications spanning larger genomic regions could be more conveniently generated and in fewer steps than using current technologies. Furthermore, the use of long regions of homology could increase the targeting frequency of "hard to target" loci in eukaryotic cells, since the targeting of homologous recombination in eukaryotic cells appears to be related to the total homology contained within the targeting vector (Deng and Capecchi, Mol Cell Biol, 12:3365–71, 1992). In addition, the increased targeting frequency obtained using long homology arms could diminish any potential benefit that can be derived from using isogenic DNA in these targeting vectors.

The problem of engineering precise modifications into very large genomic fragments, such as those cloned in BAC libraries, has largely been solved through the use of homologous recombination in bacteria (Zhang, et al., Nat Genet, 20:123–8, 1998; Yang, et al., Nat Biotechnol, 15:859–65, 1997; Angrand, et al., Nucleic Acids Res, 27:e16, 1999; Muyrers, et al., Nucleic Acids Res, 27:1555–7, 1999; Narayanan, et al., Gene Ther, 6:442–7, 1999), allowing for the construction of vectors containing large regions of homology to eukaryotic endogenous genes or chromosomal loci. However, once made, these vectors have not been generally useful for modifying endogenous genes or chromosomal loci via homologous recombination because of the difficulty in detecting rare correct targeting events when homology arms are larger than 10–20 kb (Joyner, The Practical Approach Series, 293, 1999). Consequently, vectors generated using bacterial homologous recombination from BAC genomic fragments must still be extensively trimmed prior to use as targeting vectors (Hill et al., Genomics, 64:111–3, 2000). Therefore, there is still a need for a rapid and convenient methodology that makes possible the use of targeting vectors containing large regions of homology so as to modify endogenous genes or chromosomal loci in eukaryotic cells.

In accordance with the present invention, Applicants provide novel methods that enable the use of targeting vectors containing large regions of homology so as to modify endogenous genes or chromosomal loci in eukaryotic cells via homologous recombination. Such methods overcome the above-described limitations of current technologies. In addition, the skilled artisan will readily recognize that the methods of the invention are easily adapted for use with any genomic DNA of any eukaryotic organism including, but not limited to, animals such as mouse, rat, other rodent, or human, as well as plants such as soy, corn and wheat.

SUMMARY OF THE INVENTION

In accordance with the present invention, Applicants have developed a novel, rapid, streamlined, and efficient method for creating and screening eukaryotic cells which contain modified endogenous genes or chromosomal loci. This novel methods combine, for the first time:
1. Bacterial homologous recombination to precisely engineer a desired genetic modification within a large cloned genomic fragment, thereby creating a large targeting vector for use in eukaryotic cells (LTVECs);
2. Direct introduction of these LTVECs into eukaryotic cells to modify the endogenous chromosomal locus of interest in these cells; and
3. An analysis to determine the rare eukaryotic cells in which the targeted allele has been modified as desired, involving an assay for modification of allele (MOA) of the parental allele that does not require sequence information outside of the targeting sequence, such as, for example, quantitative PCR.

A preferred embodiment of the invention is a method for genetically modifying an endogenous gene or chromosomal locus in eukaryotic cells, comprising: a) obtaining a large cloned genomic fragment containing a DNA sequence of interest; b) using bacterial homologous recombination to genetically modify the large cloned genomic fragment of (a) to create a large targeting vector for use in the eukaryotic cells (LTVEC); c) introducing the LTVEC of (b) into the eukaryotic cells to modify the endogenous gene or chromosomal locus in the cells; and d) using a quantitative assay to detect modification of allele (MOA) in the eukaryotic cells of (c) to identify those eukaryotic cells in which the endogenous gene or chromosomal locus has been genetically modified.

Another embodiment of the invention is a method wherein the genetic modification to the endogenous gene or chromosomal locus comprises deletion of a coding sequence, gene segment, or regulatory element; alteration of a coding sequence, gene segment, or regulatory element; insertion of a new coding sequence, gene segment, or regulatory element; creation of a conditional allele; or replacement of a coding sequence or gene segment from one species with an homologous or orthologous coding sequence from a different species.

An alternative embodiment of the invention is a method wherein the alteration of a coding sequence, gene segment, or regulatory element comprises a substitution, addition, or fusion, wherein the fusion comprises an epitope tag or bifunctional protein.

Yet another embodiment of the invention is a method wherein the quantitative assay comprises quantitative PCR, comparative genomic hybridization, isothermic DNA amplification, or quantitative hybridization to an immobilized probe, wherein the quantitative PCR comprises TaqMan® technology or quantitative PCR using molecular beacons.

Another preferred embodiment of the invention is a method wherein the eukaryotic cell is a mammalian embryonic stem cell and in particular wherein the embryonic stem cell is a mouse, rat, or other rodent embryonic stem cell.

Another preferred embodiment of the invention is a method wherein the endogenous gene or chromosomal locus is a mammalian gene or chromosomal locus, preferably a human gene or chromosomal locus or a mouse, rat, or other rodent gene or chromosomal locus.

An additional preferred embodiment is one in which the LTVEC is capable of accommodating large DNA fragments greater than 20 kb, and in particular large DNA fragments greater than 100 kb.

Another preferred embodiment is a genetically modified endogenous gene or chromosomal locus that is produced by the method of the invention.

Yet another preferred embodiment is a genetically modified eukaryotic cell that is produced by the method of the invention.

A preferred embodiment of the invention is a non-human organism containing the genetically modified endogenous gene or chromosomal locus produced by the method of the invention.

Also preferred in a non-human organism produced from the genetically modified eukaryotic cells or embryonic stem cells produced by the method of the invention.

A preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector (LTVEC) for use in embryonic stem cells; c) introducing the LTVEC of (b) into the embryonic stem cells to modify the endogenous gene or chromosomal locus in the cells; d) using a quantitative assay to detect modification of allele (MOA) in the embryonic stem cells of (c) to identify those embryonic stem cells in which the endogenous gene or chromosomal locus has been genetically modified; e) introducing the embryonic stem cell of (d) into a blastocyst; and f) introducing the blastocyst of (e) into a surrogate mother for gestation.

An additional preferred embodiment of the invention is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c) to identify those eukaryotic cells in which the endogenous gene or chromosomal locus has been genetically modified; e) removing the nucleus from the eukaryotic cell of (d); f) introducing the nucleus of (e) into an oocyte; and g) introducing the oocyte of (f) into a surrogate mother for gestation.

Yet another preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c) to identify those eukaryotic cells in which the endogenous gene or chromosomal locus has been genetically modified; e) fusing the eukaryotic cell of (d) with another eukaryotic cell; f) introducing the fused eukaryotic cell of (e) into a surrogate mother for gestation.

In preferred embodiments, the non-human organism is a mouse, rat, or other rodent; the blastocyst is a mouse, rat, or other rodent blastocyst; the oocyte is a mouse, rat, or other rodent oocyte; and the surrogate mother is a mouse, rat, or other rodent.

Another preferred embodiment is one in which the embryonic stem cell is a mammalian embryonic stem cell, preferably a mouse, rat, or other rodent embryonic stem cell.

An additional preferred embodiment is the use of the genetically modified eukaryotic cells of the invention for the production of a non-human organism, and in particular, the use of the genetically modified embryonic stem cell of the invention for the production of a non-human organism.

A preferred embodiment of the invention is a method for genetically modifying an endogenous gene or chromosomal locus of interest in mouse embryonic stem cells, comprising: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR. Also preferred is a genetically modified mouse embryonic stem cell produced by this method; a mouse containing a genetically modified endogenous gene or chromosomal locus produced by this method; and a mouse produced from the genetically modified mouse embryonic stem cell.

Another preferred embodiment is a mouse containing a genetically modified endogenous gene or chromosomal locus of interest, produced by a method comprising the steps of: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR; e) introducing the mouse embryonic stem cell of (d) into a blastocyst; and f) introducing the blastocyst of (e) into a surrogate mother for gestation.

Also preferred is the use of the genetically modified mouse embryonic stem cell described above for the production of a mouse.

One embodiment of the invention is a method of replacing, in whole or in part, in a non-human eukaryotic cell, an endogenous immunoglobulin variable region gene locus with an homologous or orthologous human gene locus comprising:
  a) obtaining a large cloned genomic fragment containing, in whole or in part, the homologous or orthologous human gene locus;
  b) using bacterial homologous recombination to genetically modify the cloned genomic fragment of (a) to create a large targeting vector for use in the eukaryotic cells (LTVEC);
  c) introducing the LTVEC of (b) into the eukaryotic cells to replace, in whole or in part, the endogenous immunoglobulin variable gene locus; and
  d) using a quantitative assay to detect modification of allele (MOA) in the eukaryotic cells of (c) to identify those eukaryotic cells in which the endogenous immunoglobulin variable region gene locus has been replaced, in whole or in part, with the homologous or orthologous human gene locus.

Another embodiment is a method of replacing, in whole or in part, in a non-human eukaryotic cell, an endogenous immunoglobulin variable region gene locus with an homologous or orthologous human gene locus further comprising the steps:
  e) obtaining a large cloned genomic fragment containing a part of the homologous or orthologous human gene locus that differs from the fragment of (a);
  f) using bacterial homologous recombination to genetically modify the cloned genomic fragment of (e) to create a second LTVEC;
  g) introducing the second LTVEC of (f) into the eukaryotic cells identified in step (d) to replace, in whole or in part, the endogenous immunoglobulin variable gene locus; and
  h) using a quantitative assay to detect modification of allele (MOA) in the eukaryotic cells of (g) to identify those eukaryotic cells in which the endogenous immunoglobulin variable region gene locus has been replaced, in whole or in part, with the homologous or orthologous human gene locus.

Another embodiment of the above method is a method wherein steps (e) through (h) are repeated until the endogenous immunoglobulin variable region gene locus is replaced in whole with an homologous or orthologous human gene locus.

Another embodiment of the method is one in which the immunoglobulin variable gene locus is a locus selected from the group consisting of:
  a) a variable gene locus of the kappa light chain;
  b) a variable gene locus of the lambda light chain; and
  c) a variable gene locus of the heavy chain.

A preferred embodiment is a method wherein the quantitative assay comprises quantitative PCR, FISH, comparative genomic hybridization, isothermic DNA amplification, or quantitative hybridization to an immobilized probe, and in particular wherein the quantitative PCR comprises Taq-Man® technology or quantitative PCR using molecular beacons.

Yet another preferred embodiment is a method of replacing, in whole or in part, in a mouse embryonic stem cell, an endogenous immunoglobulin variable region gene locus with its homologous or orthologous human gene locus comprising:
  a) obtaining a large cloned genomic fragment containing, in whole or in part, the homologous or orthologous human gene locus;
  b) using bacterial homologous recombination to genetically modify the large cloned genomic fragment of (a) to create a large targeting vector for use in the embryonic stem cells;
  c) introducing the large targeting vector of (b) into mouse embryonic stem cells to replace, in whole or in part, the endogenous immunoglobulin variable gene locus in the cells; and
  d) using a quantitative PCR assay to detect modification of allele (MOA) in the mouse embryonic stem cells of (d) to identify those mouse embryonic stem cells in which the endogenous variable gene locus has been replaced, in whole or in part, with the homologous or orthologous human gene locus.

In another embodiment, the method further comprises:
  e) obtaining a large cloned genomic fragment containing a part of the homologous or orthologous human gene locus that differs from the fragment of (a);
  f) using bacterial homologous recombination to genetically modify the cloned genomic fragment of (e) to create a large targeting vector for use in the embryonic stem cells;
  g) introducing the large targeting vector of (f) into the mouse embryonic stem cells identified in step (d) to replace, in whole or in part, the endogenous immunoglobulin variable gene locus; and
  h) using a quantitative assay to detect modification of allele (MOA) in the mouse embryonic stem cells of (g) to identify those mouse embryonic stem cells in which the endogenous immunoglobulin variable region gene locus has been replaced, in whole or in part, with the homologous or orthologous human gene locus.

Still another preferred embodiment is a method of wherein steps (e) through (h) above are repeated until the endogenous immunoglobulin variable region gene locus is replaced in whole with an homologous or orthologous human gene locus.

Also preferred is a method wherein the immunoglobulin variable gene locus comprises a locus selected from the group consisting of
  a) a variable gene locus of the kappa light chain;
  b) a variable gene locus of the lambda light chain; and
  c) a variable gene locus of the heavy chain.

Another preferred embodiment is a genetically modified immunoglobulin variable region gene locus produced by the methods described above; a genetically modified eukaryotic cell comprising a genetically modified immunoglobulin variable region gene locus produced by the methods described above; a non-human organism comprising a genetically modified immunoglobulin variable region gene locus produced by the methods described above; and a mouse embryonic stem cell containing a genetically modified immunoglobulin variable region gene locus produced by the methods described above.

Also preferred is an embryonic stem cell wherein the mouse heavy chain variable region locus is replaced, in whole or in part, with a human heavy chain variable gene locus; an embryonic stem cell of claim wherein the mouse kappa light chain variable region locus is replaced, in whole or in part, with a human kappa light chain variable region locus; an embryonic stem cell wherein the mouse lambda light chain variable region locus is replaced, in whole or in part, with a human lambda light chain variable region locus; and an embryonic stem cell wherein the heavy and light chain variable region gene loci are replaced, in whole, with their human homologs or orthologs.

Another preferred embodiment is a mouse produced from the embryonic stem cells described above.

Yet another preferred embodiment is an antibody comprising a human variable region encoded by the genetically modified variable gene locus of described above; an antibody further comprising a non-human constant region; and an antibody further comprising a human constant region.

Also preferred is a transgenic mouse having a genome comprising entirely human heavy and light chain variable region loci operably linked to entirely endogenous mouse constant region loci such that the mouse produces a serum containing an antibody comprising a human variable region and a mouse constant region in response to antigenic stimulation; a transgenic mouse having a genome comprising human heavy and/or light chain variable region loci operably linked to endogenous mouse constant region loci such that the mouse produces a serum containing an antibody comprising a human variable region and a mouse constant region in response to antigenic stimulation; a transgenic mouse containing an endogenous variable region locus that has been replaced with an homologous or orthologous human variable locus, such mouse being produced by a method comprising:
  a) obtaining one or more large cloned genomic fragments containing the entire homologous or orthologous human variable region locus;
  b) using bacterial homologous recombination to genetically modify the cloned genomic fragment(s) of (a) to create large targeting vector(s) for use in mouse embryonic stem cells;
  c) introducing the large targeting vector(s) of (b) into mouse embryonic stem cells to replace the entire endogenous variable region locus in the cells; and
  d) using a quantitative PCR assay to detect modification of allele (MOA) in the mouse embryonic stem cells of (c) to identify those mouse embryonic stem cells in which the entire endogenous variable region locus has been replaced with the homologous or orthologous human variable region locus;
  e) introducing the mouse embryonic stem cell of (d) into a blastocyst; and
  f) introducing the blastocyst of (e) into a surrogate mother for gestation.

Another preferred embodiment is a transgenic mouse described above wherein the immunoglobulin variable region gene locus comprises one or more loci selected from the group consisting of:
  a) a variable gene locus of the kappa light chain;
  b) a variable gene locus of the lambda light chain; and
  c) a variable gene locus of the heavy chain.

Also preferred are the methods described above wherein the mouse embryonic stem cell is derived from a transgenic mouse produced by the methods.

Still yet another preferred embodiment of the invention is a method of making a human antibody comprising:

a) exposing the mouse described above to antigenic stimulation, such that the mouse produces an antibody against the antigen;
b) isolating the DNA encoding the variable regions of the heavy and light chains of the antibody;
c) operably linking the DNA encoding the variable regions of (b) to DNA encoding the human heavy and light chain constant regions in a cell capable of expressing active antibodies;
d) growing the cell under such conditions as to express the human antibody; and
e) recovering the antibody.

In another preferred embodiment, the cell described above is a CHO cell.

Also preferred is a method of wherein the DNA of step (b) described above is isolated from a hybridoma created from the spleen of the mouse exposed to antigenic stimulation in step (a) described above.

Also preferred is the method described above wherein the DNA is isolated by PCR.

Another preferred embodiment is a method of replacing, in whole or in part, an endogenous immunoglobulin variable region gene locus with an homologous or orthologous gene locus comprising:
a) creating a LTVEC comprising a site-specific recombination site, a downstream homology arm containing the region immediately adjacent to, but not including, the J segments of the immunoglobulin variable gene locus region and an upstream homology arm within the variable gene locus;
b) creating a LTVEC comprising a site-specific recombination site, an upstream homology arm containing the region adjacent to the most distal V gene segment, but not containing any V gene segments of the immunoglobulin variable gene locus region and a downstream homology arm within the variable gene locus;
c) introducing the LTVEC s of (a) and (b) into the eukaryotic cell;
d) using a quantitative assay to detect modification of allele (MOA) in the variable gene locus to identify those eukaryotic cells in (c) in which the site-specific recombination sites flank the endogenous variable region gene locus;
e) creating a vector containing the site-specific recombination sequences flanking all or part of the orthologous or homologous gene locus; and
f) introducing the vector of (e) into the eukaryotic cells identified in step (d) such that, through recombination, the endogenous immunoglobulin variable region gene locus is replaced, in whole or in part, with the homologous or orthologous gene locus.

Also preferred is a transgenic mouse containing an endogenous immunoglobulin variable region locus that has been replaced with an homologous or orthologous human immunoglobulin variable region locus, such mouse being produced by a method comprising:
a) creating a LTVEC comprising a site-specific recombination site and a downstream homology arm containing the region immediately adjacent to, but not including, the J segments of the mouse immunoglobulin variable gene locus region;
b) creating a LTVEC comprising a site-specific recombination site and an upstream homology arm containing the region adjacent to the most distal mouse V gene segment, but not containing any V gene segments of the mouse immunoglobulin variable gene locus region;
c) introducing the LTVEC s of (a) and (b) into the eukaryotic cell; using a quantitative assay to detect modification of allele (MOA) in the variable gene locus to identify those eukaryotic cells in (c) in which the site-specific recombination sites flank the endogenous immunoglobulin variable region gene locus;
d) creating a vector containing the site-specific recombination sequences flanking all or part of the orthologous or homologous gene locus;
e) introducing the vector of (e) into the eukaryotic cells identified in step (d) such that, through recombination, the endogenous immunoglobulin variable region gene locus is replaced, in whole or in part, with the homologous or orthologous gene locus;
f) introducing the mouse embryonic stem cell of (d) into a blastocyst;; and introducing the blastocyst of (e) into a surrogate mother for gestation.

Yet another preferred embodiment is a method of creating, in a eukaryotic cell, an endogenous gene locus flanked downstream by a site-specific recombination site comprising:
a) creating a LTVEC comprising the site-specific recombination site, a downstream homology arm containing a region that flanks the 3' end of the endogenous gene locus region and an upstream homology arm within the locus;
b) introducing the LTVEC of (a) into the eukaryotic cell; and
c) using a quantitative assay to detect modification of allele (MOA) in the endogenous gene locus to identify those eukaryotic cells in (b) in which the endogenous gene locus is flanked downstream by the site-specific recombination site.

Still another preferred embodiment is a method of creating, in a eukaryotic cell, an endogenous gene locus flanked upstream by a site-specific recombination site comprising:
a) creating a LTVEC comprising the site-specific recombination site, an upstream homology arm containing a region that flanks the 5' end of the endogenous gene locus region and a downstream homology arm within the locus;
b) introducing the LTVEC of (a) into the eukaryotic cell; and
c) using a quantitative assay to detect modification of allele (MOA) in the endogenous gene locus to identify those eukaryotic cells in (b) in which the endogenous gene locus is flanked upstream by the site-specific recombination site.

Also preferred is a method of creating, in a eukaryotic cell, an endogenous gene locus flanked by site-specific recombination sites comprising:
a) creating a LTVEC comprising the site-specific recombination site, a downstream homology arm containing a region that flanks the 3' end of the endogenous gene locus region and an upstream homology arm within the locus;
b) creating a LTVEC comprising the site-specific recombination site, an upstream homology arm containing a region that flanks the 5' end of the endogenous gene locus region and a downstream homology arm within the locus;
c) introducing the LTVEC's of (a) and (b) into the eukaryotic cell; and
d) using a quantitative assay to detect modification of allele (MOA) in the endogenous gene locus to identify those eukaryotic cells in (c) in which the site-specific recombination sites are flanking the endogenous gene locus.

Still another preferred embodiment is a method of creating, in a eukaryotic cell, an endogenous immunoglobulin variable gene locus flanked by a site-specific recombination site comprising:
a) creating a LTVEC comprising a site-specific recombination site, a downstream homology arm containing the region immediately adjacent to, but not including, the J segments of the immunoglobulin variable gene locus region and an upstream homology arm within the variable gene locus;

b) introducing the LTVEC of (a) into the eukaryotic cell; and
c) using a quantitative assay to detect modification of allele (MOA) in the variable gene locus to identify those eukaryotic cells in (b) in which the site-specific recombination site flanks the downstream end of the endogenous immunovariable variable gene locus.

Also preferred is a method of creating, in a eukaryotic cell, an endogenous immunoglobulin variable gene locus flanked by site-specific recombination sites comprising:
a) creating a LTVEC comprising a site-specific recombination site, an upstream homology arm containing the region adjacent to the most distal V gene segment, but not containing any V gene segments of the immunoglobulin variable gene locus region, and a downstream homology arm within the locus;
b) introducing the LTVEC of (a) into the eukaryotic cell; and
c) using a quantitative assay to detect modification of allele (MOA) in the variable gene locus to identify those eukaryotic cells in (c) in which the site-specific recombination sites flank the upstream end of the endogenous immunoglobulin variable region gene locus.

Still another embodiment is a method of creating, in a eukaryotic cell, an endogenous immunoglobulin variable gene locus flanked by site-specific recombination sites comprising:
a) creating a LTVEC comprising a site-specific recombination site, a downstream homology arm containing the region immediately adjacent to, but not including, the J segments of the immunoglobulin variable gene locus region, and an upstream homology arm within the locus;
b) creating a LTVEC comprising a site-specific recombination site, an upstream homology arm containing the region adjacent to the most distal V gene segment, but not containing any V gene segments of the immunoglobulin variable gene locus region, and a downstream arm within the locus;
c) introducing the LTVECs of (a) and (b) into the eukaryotic cell; and
d) using a quantitative assay to detect modification of allele (MOA) in the variable gene locus to identify those eukaryotic cells in (c) in which the site-specific recombination sites flank the endogenous immunoglobulin variable region gene locus.

BRIEF DESCRIPTION OF THE FIGURES

FIG. 3A–3D: Sequence of the mouse OCR10 cDNA and mouse OCR10 amino acid sequence (SEQ ID NO:6), homology box 1 (hb1), homology box 2 (hb2), and TaqMan® probes and primers used in a quantitative PCR assay to detect modification of allele (MOA) in ES cells targeted using the mOCR10LTVEC.
hb1: base pairs 1 to 211
hb2: base pairs 1586 to 1801
TaqMan® probe and corresponding PCR primer set derived from mOCR10 exon 3:
  TaqMan® probe: nucleotides 413 to 439—upper strand
  Primer ex3-5': nucleotides 390 to 410—upper strand
  Primer ex3-3': nucleotides 445 to 461—lower strand
TaqMan® probe and corresponding PCR primer set derived from mOCR10 exon 4:
  TaqMan® probe: nucleotides 608 to 639—upper strand
  Primer ex4-5': nucleotides 586 to 605—upper strand
  Primer ex4-3': nucleotides 642 to 662—lower strand FIG. 4A–4D: Schematic diagram of the two LTVECs constructed to replace the mouse VDJ region with human VDJ region.

FIG. 4A: Large insert (BAC) clones spanning the entire VDJ region of the human heavy chain locus are isolated.

FIG. 4B: In this example, large insert (BAC) clones are isolated from the ends of the mouse VDJ region as a source of homology arms which are used to direct integration via homologous recombination of the human VDJ sequences in a two step process.

FIG. 4C–4D: In the first step, LTVEC1 (FIG. 4D) is constructed by bacterial homologous recombination in E. coli. LTVEC1 contains, in order: a large mouse homology arm derived from the region upstream from the mouse DJ region, but whose absolute endpoints are not important; a cassette encoding a selectable marker functional in ES cells (PGK-neomycinR in this example); a loxP site; a large human insert spanning from several V gene segments through the entire DJ region; and a mouse homology arm containing the region immediately adjacent to, but not including, the mouse J segments. In the second step, LTVEC2 (FIG. 4C) is constructed by bacterial homologous recombination in E. coli. LTVEC2 contains, in order: a large mouse homology arm containing the region adjacent to the most distal mouse V gene segment, but not containing any mouse V gene segments; a large insert containing a large number of distal human V gene segments; a mutant loxP site called lox511 in the orientation opposite to that of the wild type loxP sites in LTVEC2 and LTVEC1 (this site will not recombine with wild type loxP sites but will readily recombine with other lox511 sites); a wild type loxP site; a second selectable marker (PGK-hygromycinR in this example); and a mouse homology arm derived from the V region, but whose absolute endpoints are not important.

DEFINITIONS

Figure 1:
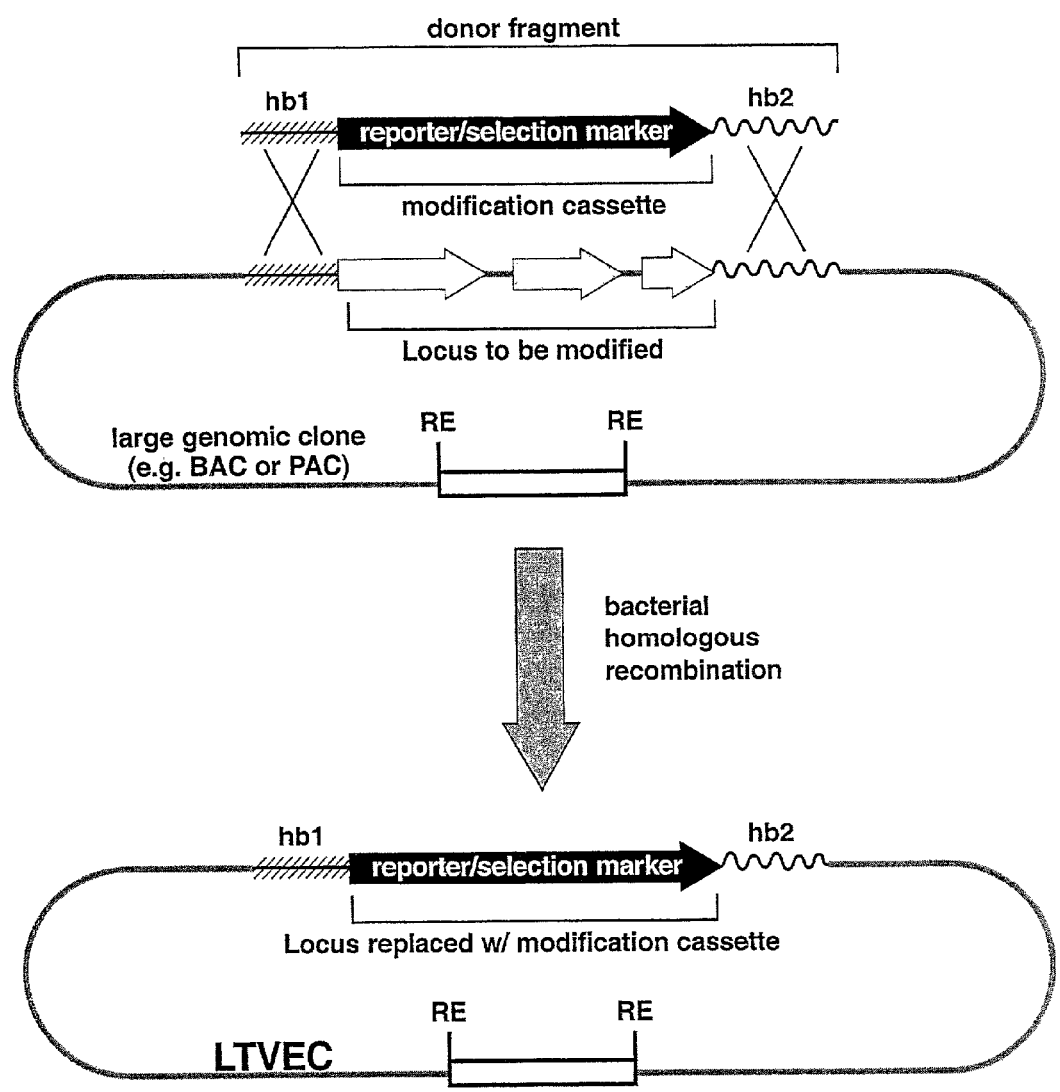
FIG. 1: Schematic diagram of the generation of a typical LTVEC using bacterial homologous recombination.
(hb1=homology box 1; hb2=homology box 2; RE=restriction enzyme site).

A "targeting vector" is a DNA construct that contains sequences "homologous" to endogenous chromosomal nucleic acid sequences flanking a desired genetic modification(s). The flanking homology sequences, referred to as "homology arms", direct the targeting vector to a specific chromosomal location within the genome by virtue of the homology that exists between the homology arms and the corresponding endogenous sequence and introduce the desired genetic modification by a process referred to as "homologous recombination".

"Homologous" means two or more nucleic acid sequences that are either identical or similar enough that they are able to hybridize to each other or undergo intermolecular exchange.

"Gene targeting" is the modification of an endogenous chromosomal locus by the insertion into, deletion of, or replacement of the endogenous sequence via homologous recombination using a targeting vector.

A "gene knockout" is a genetic modification resulting from the disruption of the genetic information encoded in a chromosomal locus.

A "gene knockin" is a genetic modification resulting from the replacement of the genetic information encoded in a chromosomal locus with a different DNA sequence.

A "knockout organism" is an organism in which a significant proportion of the organism's cells harbor a gene knockout.

A "knockin organism" is an organism in which a significant proportion of the organism's cells harbor a gene knockin.

A "marker" or a "selectable marker" is a selection marker that allows for the isolation of rare transfected cells expressing the marker from the majority of treated cells in the population. Such marker's gene's include, but are not limited to, neomycin phosphotransferase and hygromycin B phosphotransferase, or fluorescing proteins such as GFP.

An "ES cell" is an embryonic stem cell. This cell is usually derived from the inner cell mass of a blastocyst-stage embryo.

An "ES cell clone" is a subpopulation of cells derived from a single cell of the ES cell population following introduction of DNA and subsequent selection.

A "flanking DNA" is a segment of DNA that is collinear with and adjacent to a particular point of reference.

"LTVECs" are large targeting vectors for eukaryotic cells that are derived from fragments of cloned genomic DNA larger than those typically used by other approaches intended to perform homologous targeting in eukaryotic cells.

A "non-human organism" is an organism that is not normally accepted by the public as being human.

"Modification of allele" (MOA) refers to the modification of the exact DNA sequence of one allele of a gene(s) or chromosomal locus (loci) in a genome. This modification of allele (MOA) includes, but is not limited to, deletions, substitutions, or insertions of as little as a single nucleotide or deletions of many kilobases spanning a gene(s) or chromosomal locus (loci) of interest, as well as any and all possible modifications between these two extremes.

"Orthologous" sequence refers to a sequence from one species that is the functional equivalent of that sequence in another species.

The description and examples presented infra are provided to illustrate the subject invention. One of skill in the art will recognize that these examples are provided by way of illustration only and are not included for the purpose of limiting the invention.

DETAILED DESCRIPTION OF THE INVENTION

Applicants have developed a novel, rapid, streamlined, and efficient method for creating and screening eukaryotic cells which contain modified endogenous genes or chromosomal loci. In these cells, the modification may be gene(s) knockouts, knockins, point mutations, or large genomic insertions or deletions or other modifications. By way of non-limiting example, these cells may be embryonic stem cells which are useful for creating knockout or knockin organisms and in particular, knockout or knockin mice, for the purpose of determining the function of the gene(s) that have been altered, deleted and/or inserted.

The novel methods described herein combine, for the first time:

1. Bacterial homologous recombination to precisely engineer a desired genetic modification within a large cloned genomic DNA fragment, thereby creating a large targeting vector for use in eukaryotic cells (LTVECs);
2. Direct introduction of these LTVECs into eukaryotic cells to modify the corresponding endogenous gene(s) or chromosomal locus(loci) of interest in these cells; and
3. An analysis to determine the rare eukaryotic cells in which the targeted allele has been modified as desired, involving a quantitative assay for modification of allele (MOA) of the parental allele.

It should be emphasized that previous methods to detect successful homologous recombination in eukaryotic cells cannot be utilized in conjunction with the LTVECs of Applicants' invention because of the long homology arms present in the LTVECs. Utilizing a LTVEC to deliberately modify endogenous genes or chromosomal loci in eukaryotic cells via homologous recombination is made possible by the novel application of an assay to determine the rare eukaryotic cells in which the targeted allele has been modified as desired, such assay involving a quantitative assay for modification of allele (MOA) of a parental allele, by employing, for example, quantitative PCR or other suitable quantitative assays for MOA.

The ability to utilize targeting vectors with homology arms larger than those used in current methods is extremely valuable for the following reasons:

1. Targeting vectors are more rapidly and conveniently generated from available libraries containing large genomic inserts (e.g. BAC or PAC libraries) than targeting vectors made using previous technologies, in which the genomic inserts have to be extensively characterized and "trimmed" prior to use (explained in detail below). In addition, minimal sequence information needs to be known about the locus of interest, i.e. it is only necessary to know the approximately 80–100 nucleotides that are required to generate the homology boxes (described in detail below) and to generate probes that can be used in quantitative assays for MOA (described in detail below).
2. Larger modifications as well as modifications spanning larger genomic regions are more conveniently generated and in fewer steps than using previous technologies. For example, the method of the invention makes possible the precise modification of large loci that cannot be accommodated by traditional plasmid-based targeting vectors because of their size limitations. It also makes possible the modification of any given locus at multiple points (e.g. the introduction of specific mutations at different exons of a multi-exon gene) in one step, alleviating the need to engineer multiple targeting vectors and to perform multiple rounds of targeting and screening for homologous recombination in ES cells.
3. The use of long regions of homology (long homology arms) increase the targeting frequency of "hard to target" loci in eukaryotic cells, consistent with previous findings that targeting of homologous recombination in eukaryotic cells appears to be related to the total homology contained within the targeting vector.

4. The increased targeting frequency obtained using long homology arms apparently diminishes the benefit, if any, from using isogenic DNA in these targeting vectors.

5. The application of quantitative MOA assays for screening eukaryotic cells for homologous recombination not only empowers the use of LTVECs as targeting vectors (advantages outlined above) but also reduces the time for identifying correctly modified eukaryotic cells from the typical several days to a few hours. In addition, the application of quantitative MOA does not require the use of probes located outside the endogenous gene(s) or chromosomal locus(loci) that is being modified, thus obviating the need to know the sequence flanking the modified gene(s) or locus(loci). This is a significant improvement in the way the screening has been performed in the past and makes it a much less labor-intensive and much more cost-effective approach to screening for homologous recombination events in eukaryotic cells.

METHODS

Many of the techniques used to construct DNA vectors described herein are standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, NY). All DNA sequencing is done by standard techniques using an ABI 373A DNA sequencer and Taq Dideoxy Terminator Cycle Sequencing Kit (Applied Biosystems, Inc., Foster City, Calif.).

Step 1. Obtain a Large Genomic DNA Clone Containing the Gene(s) or Chromosomal Locus (Loci) of Interest.

A gene(s) or locus(loci) of interest can be selected based on specific criteria, such as detailed structural or functional data, or it can be selected in the absence of such detailed information as potential genes or gene fragments become predicted through the efforts of the various genome sequencing projects. Importantly, it should be noted that it is not necessary to know the complete sequence and gene structure of a gene(s) of interest to apply the method of the subject invention to produce LTVECs. In fact, the only sequence information that is required is approximately 80–100 nucleotides so as to obtain the genomic clone of interest as well as to generate the homology boxes used in making the LTVEC (described in detail below) and to make probes for use in quantitative MOA assays.

Once a gene(s) or locus(loci) of interest has been selected, a large genomic clone(s) containing this gene(s) or locus (loci) is obtained. This clone(s) can be obtained in any one of several ways including, but not limited to, screening suitable DNA libraries (e.g. BAC, PAC, YAC, or cosmid) by standard hybridization or PCR techniques, or by any other methods familiar to the skilled artisan.

Step 2. Append Homology Boxes 1 and 2 to a Modification Cassette and Generation of LTVEC.

Homology boxes mark the sites of bacterial homologous recombination that are used to generate LTVECs from large cloned genomic fragments (FIG. 1). Homology boxes are short segments of DNA, generally double-stranded and at least 40 nucleotides in length, that are homologous to regions within the large cloned genomic fragment flanking the "region to be modified". The homology boxes are appended to the modification cassette, so that following homologous recombination in bacteria, the modification cassette replaces the region to be modified (FIG. 1). The technique of creating a targeting vector using bacterial homologous recombination can be performed in a variety of systems (Yang et al., Nat Biotechnol, 15:859–65, 1997; Muyrers et al., Nucleic Acids Res, 27:1555–7, 1999; Angrand et al., Nucleic Acids Res, 27:e16, 1999; Narayanan et al., Gene Ther, 6:442–7, 1999; Yu, et al., Proc Natl Acad Sci USA, 97:5978–83, 2000). One example of a favored technology currently in use is ET cloning (Zhang et al., Nat Genet, 20:123–8, 1998; Narayanan et al., Gene Ther, 6:442–7, 1999) and variations of this technology (Yu, et al., Proc Natl Acad Sci USA, 97:5978–83, 2000). ET refers to the recE (Hall and Kolodner, Proc Natl Acad Sci USA, 91:3205–9, 1994) and recT proteins (Kusano et al., Gene, 138:17–25, 1994) that carry out the homologous recombination reaction. RecE is an exonuclease that trims one strand of linear double-stranded DNA (essentially the donor DNA fragment described infra) 5' to 3', thus leaving behind a linear double-stranded fragment with a 3' single-stranded overhang. This single-stranded overhang is coated by recT protein, which has single-stranded DNA (ssDNA) binding activity (Kovall and Matthews, Science, 277:1824–7, 1997). ET cloning is performed using E. coli that transiently express the E. coli gene products of recE and recT (Hall and Kolodner, Proc Natl Acad Sci USA, 91:3205–9, 1994; Clark et al., Cold Spring Harb Symp Quant Biol, 49:453–62, 1984; Noirot and Kolodner, J Biol Chem, 273:12274–80, 1998; Thresher et al., J Mol Biol, 254:364–71, 1995; Kolodner et al., Mol Microbiol, 11:23–30, 1994; Hall et al., J Bacteriol, 175:277–87, 1993) and the bacteriophage lambda (λ) protein λgam (Murphy, J Bacteriol, 173:5808–21, 1991; Poteete et al., J Bacteriol, 170:2012–21, 1988). The λgam protein is required for protecting the donor DNA fragment from degradation by the recBC exonuclease system (Myers and Stahl, Annu Rev Genet, 28:49–70, 1994) and it is required for efficient ET-cloning in recBC$^+$ hosts such as the frequently used E. coli strain DH10b.

The region to be modified and replaced using bacterial homologous recombination can range from zero nucleotides in length (creating an insertion into the original locus) to many tens of kilobases (creating a deletion and/or a replacement of the original locus). Depending on the modification cassette, the modification can result in the following:

(a) deletion of coding sequences, gene segments, or regulatory elements;

(b) alteration(s) of coding sequence, gene segments, or regulatory elements including substitutions, additions, and fusions (e.g. epitope tags or creation of bifunctional proteins such as those with GFP);

(c) insertion of new coding regions, gene segments, or regulatory elements, such as those for selectable marker genes or reporter genes or putting new genes under endogenous transcriptional control;

(d) creation of conditional alleles, e.g. by introduction of loxP sites flanking the region to be excised by Cre recombinase (Abremski and Hoess, J Biol Chem, 259: 1509–14, 1984), or FRT sites flanking the region to be excised by Flp recombinase (Andrews et al., Cell, 40:795–803, 1985; Meyer-Leon et al., Cold Spring Harb Symp Quant Biol, 49:797–804, 1984; Cox, Proc Natl Acad Sci USA, 80:4223–7, 1983); or (e) replacement of coding sequences or gene segments from one species with orthologous coding sequences from a different species, e.g. replacing a murine genetic locus with the orthologous human genetic locus to engineer a mouse where that particular locus has been 'humanized'.

Any or all of these modifications can be incorporated into a LTVEC. A specific, non-limiting example in which an endogenous coding sequence is entirely deleted and simultaneously replaced with both a reporter gene as well as a selectable marker is provided below in Example 1, as are the advantages of the method of the invention as compared to previous technologies.

Step 3 (optional). Verify that each LTVEC has been engineered correctly.

Verify that each LTVEC has been engineered correctly by:
a. Diagnostic PCR to verify the novel junctions created by the introduction of the donor fragment into the gene(s) or chromosomal locus(loci) of interest. The PCR fragments thus obtained can be sequenced to further verify the novel junctions created by the introduction of the donor fragment into the gene(s) or chromosomal locus (loci) of interest.
b. Diagnostic restriction enzyme digestion to make sure that only the desired modifications have been introduced into the LTVEC during the bacterial homologous recombination process.
c. Direct sequencing of the LTVEC, particularly the regions spanning the site of the modification to verify the novel junctions created by the introduction of the donor fragment into the gene(s) or chromosomal locus (loci) of interest.

Step 4. Purification, Preparation, and Linearization of LTVEC DNA for Introduction into Eukaryotic Cells.

a. Preparation of LTVEC DNA:

Prepare miniprep DNA (Sambrook, J., E. F. Fritsch And T. Maniatis. Molecular Cloning: A Laboratory Manual, Second Edition, Vols 1, 2, and 3, 1989; Tillett and Neilan, Biotechniques, 24:568–70, 572, 1998; http://www.qiagen-.com/literature/handbooks/plkmini/plm_399.pdf) of the selected LTVEC and re-transform the miniprep LTVEC DNA into E. coli using electroporation (Sambrook, J., E. F. Fritsch and T. Maniatis, Molecular Cloning: A Laboratory Manual, Second Edition, Vols 1, 2, and 3, 1989). This step is necessary to get rid of the plasmid encoding the recombinogenic proteins that are utilized for the bacterial homologous recombination step (Zhang et al., Nat Genet, 20:123–8, 1998; Narayanan et al., Gene Ther, 6:442–7, 1999). It is useful to get rid of this plasmid (a) because it is a high copy number plasmid and may reduce the yields obtained in the large scale LTVEC preps; (b) to eliminate the possibility of inducing expression of the recombinogenic proteins; and (c) because it may obscure physical mapping of the LTVEC. Before introducing the LTVEC into eukaryotic cells, larger amounts of LTVEC DNA are prepared by standard methodology (http://www.qiagen.com/literature/handbooks/plk/plklow.pdf; Sambrook, J., E. F. Fritsch And T. Maniatis. Molecular Cloning: A Laboratory Manual, Second Edition, Vols 1, 2, and 3, 1989; Tillett and Neilan, Biotechniques, 24:568–70, 572, 1998). However, this step can be bypassed if a bacterial homologous recombination method that utilizes a recombinogenic prophage is used, i.e. where the genes encoding the recombinogenic proteins are integrated into the bacterial chromosome (Yu, et al., Proc Natl Acad Sci USA, 97:5978–83, 2000), is used.

b. Linearizing the LTVEC DNA:

To prepare the LTVEC for introduction into eukaryotic cells, the LTVEC is preferably linearized in a manner that leaves the modified endogenous gene(s) or chromosomal locus(loci) DNA flanked with long homology arms. This can be accomplished by linearizing the LTVEC, preferably in the vector backbone, with any suitable restriction enzyme that digests only rarely. Examples of suitable restriction enzymes include NotI, PacI, SfiI, SrfI, SwaI, FseI, etc. The choice of restriction enzyme may be determined experimentally (i.e. by testing several different candidate rare cutters) or, if the sequence of the LTVEC is known, by analyzing the sequence and choosing a suitable restriction enzyme based on the analysis. In situations where the LTVEC has a vector backbone containing rare sites such as CosN sites, then it can be cleaved with enzymes recognizing such sites, for example λterminase (Shizuya et al., Proc Natl Acad Sci USA, 89:8794–7, 1992; Becker and Gold, Proc Natl Acad Sci USA, 75:4199–203, 1978; Rackwitz et al., Gene, 40:259–66, 1985).

Step 5. Introduction of LTVEC into Eukaryotic Cells and Selection of Cells where Successful Introduction of the LTVEC has Taken Place.

LTVEC DNA can be introduced into eukaryotic cells using standard methodology, such as transfection mediated by calcium phosphate, lipids, or electroporation (Sambrook, J., E. F. Fritsch And T. Maniatis. Molecular Cloning: A Laboratory Manual, Second Edition, Vols 1, 2, and 3, 1989). The cells where the LTVEC has been introduced successfully can be selected by exposure to selection agents, depending on the selectable marker gene that has been engineered into the LTVEC. As a non-limiting example, if the selectable marker is the neomycin phosphotransferase (neo) gene (Beck, et al., Gene, 19:327–36, 1982), then cells that have taken up the LTVEC can be selected in G418-containing media; cells that do not have the LTVEC will die whereas cells that have taken up the LTVEC will survive (Santerre, et al., Gene, 30:147–56, 1984). Other suitable selectable markers include any drug that has activity in eukaryotic cells (Joyner, The Practical Approach Series, 293, 1999), such as hygromycin B (Santerre, et al., Gene, 30:147–56, 1984; Bernard, et al., Exp Cell Res, 158:237–43, 1985; Giordano and McAllister, Gene, 88:285–8, 1990), Blasticidin S (Izumi, et al., Exp Cell Res, 197:229–33, 1991), and other which are familiar to those skilled in the art.

Step 6. Screen for Homologous Recombination Events in Eukaryotic Cells Using Quantitative Assay for Modification of Allele (MOA).

Eukaryotic cells that have been successfully modified by targeting the LTVEC into the locus of interest can be identified using a variety of approaches that can detect modification of allele within the locus of interest and that do not depend on assays spanning the entire homology arm or arms. Such approaches can include but are not limited to:

(a) quantitative PCR using TaqMan® (Lie and Petropoulos, Curr Opin Biotechnol, 9:43–8, 1998);
(b) quantitative MOA assay using molecular beacons (Tan, et al., Chemistry, 6:1107–11, 2000)
(c) fluorescence in situ hybridization FISH (Laan, et al., Hum Genet, 96:275–80, 1995) or comparative genomic hybridization (CGH) (Forozan, et al., Trends Genet, 13:405–9, 1997; Thompson and Gray, J Cell Biochem Suppl, 139–43, 1993; Houldsworth and Chaganti, Am J Pathol, 145:1253–60, 1994);
(d) isothermic DNA amplification (Lizardi, et al., Nat Genet, 19:225–32, 1998; Mitra and Church, Nucleic Acids Res, 27:e34, 1999); and (e) quantitative hybridization to an immobilized probe(s) (Southern, J. Mol. Biol. 98: 503, 1975; Kafatos FC; Jones CW; Efstratiadis A, Nucleic Acids Res 7(6): 1541–52, 1979).

Applicants provide herein an example in which TaqMan® quantitative PCR is used to screen for successfully targeted eukaryotic cells. In this non limiting example, TaqMan® is used to identify eukaryotic cells which have undergone homologous recombination wherein a portion of one of two endogenous alleles in a diploid genome has been replaced by another sequence. In contrast to traditional methods, in which a difference in restriction fragment length spanning the entire homology arm or arms indicates the modification of one of two alleles, the quantitative TaqMan® method will detect the modification of one allele by measuring the reduction in copy number (by half) of the unmodified allele. Specifically, the probe detects the unmodified allele and not the modified allele. Therefore, the method is independent of the exact nature of the modification and not limited to the sequence replacement described in this example. TaqMan is used to quantify the number of copies of a DNA template in a genomic DNA sample, especially by comparison to a reference gene (Lie and Petropoulos, Curr Opin Biotechnol, 9:43–8, 1998). The reference gene is quantitated in the same genomic DNA as the target gene(s) or locus(loci). Therefore, two TaqMan® amplifications (each with its respective probe) are performed. One TaqMan® probe determines the "Ct" (Threshold Cycle) of the reference gene, while the other probe determines the Ct of the region of the targeted gene(s) or locus(loci) which is replaced by successful targeting. The Ct is a quantity that reflects the amount of starting DNA for each of the TaqMan® probes, i.e. a less abundant sequence requires more cycles of PCR to reach the threshold cycle. Decreasing by half the number of copies of the template sequence for a TaqMan® reaction will result in an increase of about one Ct unit. TaqMan® reactions in cells where one allele of the target gene(s) or locus(loci) has been replaced by homologous recombination will result in an increase of one Ct for the target TaqMan® reaction without an increase in the Ct for the reference gene when compared to DNA from non-targeted cells. This allows for ready detection of the modification of one allele of the gene(s) of interest in eukaryotic cells using LTVECs.

As stated above, modification of allele (MOA) screening is the use of any method that detects the modification of one allele to identify cells which have undergone homologous recombination. It is not a requirement that the targeted alleles be identical (homologous) to each other, and in fact, they may contain polymorphisms, as is the case in progeny resulting from crossing two different strains of mice. In addition, one special situation that is also covered by MOA screening is targeting of genes which are normally present as a single copy in cells, such as some of the located on the sex chromosomes and in particular, on the Y chromosome. In this case, methods that will detect the modification of the single targeted allele, such as quantitative PCR, Southern blottings, etc., can be used to detect the targeting event. It is clear that the method of the invention can be used to generate modified eukaryotic cells even when alleles are polymorphic or when they are present in a single copy in the targeted cells.

Step 8. Uses of Genetically Modified Eukaryotic Cells.

(a) The genetically modified eukaryotic cells generated by the methods described in steps 1 through 7 can be employed in any in vitro or in vivo assay, where changing the phenotype of the cell is desirable.

(b) The genetically modified eukaryotic cell generated by the methods described in steps 1 through 7 can also be used to generate an organism carrying the genetic modification. The genetically modified organisms can be generated by several different techniques including but not limited to:

1. Modified embryonic stem (ES) cells such as the frequently used rat and mouse ES cells. ES cells can be used to create genetically modified rats or mice by standard blastocyst injection technology or aggregation techniques (Robertson, Practical Approach Series, 254, 1987; Wood, et al., Nature, 365:87–9, 1993; Joyner, The Practical Approach Series, 293, 1999), tetraploid blastocyst injection (Wang, et al., Mech Dev, 62:137–45, 1997), or nuclear transfer and cloning (Wakayama, et al., Proc Natl Acad Sci USA, 96:14984–9, 1999). ES cells derived from other organisms such as rabbits (Wang, et al., Mech Dev, 62:137–45, 1997; Schoonjans, et al., Mol Reprod Dev, 45:439–43, 1996) or chickens (Pain, et al., Development, 122:2339–48, 1996) or other species should also be amenable to genetic modification(s) using the methods of the invention.

2. Modified protoplasts can be used to generate genetically modified plants (for example see U.S. Pat. No. 5,350,689 "Zea mays plants and transgenic Zea mays plants regenerated from protoplasts or protoplast-derived cells", and U.S. Pat. No. 5,508,189 "Regeneration of plants from cultured guard cell protoplasts" and references therein).

3. Nuclear transfer from modified eukaryotic cells to oocytes to generate cloned organisms with modified allele (Wakayama, et al., Proc Natl Acad Sci USA, 96:14984–9, 1999; Baguisi, et al., Nat Biotechnol, 17:456–61, 1999; Wilmut, et al., Reprod Fertil Dev, 10:639–43, 1998; Wilmut, et al., Nature, 385:810–3, 1997; Wakayama, et al., Nat Genet, 24:108–9, 2000; Wakayama, et al., Nature, 394:369–74, 1998; Rideout, et al., Nat Genet, 24:109–10, 2000; Campbell, et al., Nature, 380:64–6, 1996).

4. Cell-fusion to transfer the modified allele to another cell, including transfer of engineered chromosome(s), and uses of such cell(s) to generate organisms carrying the modified allele or engineered chromosome(s) (Kuroiwa, et al., Nat Biotechnol, 18:1086–1090, 2000).

5. The method of the invention are also amenable to any other approaches that have been used or yet to be discovered.

While many of the techniques used in practicing the individual steps of the methods of the invention are familiar to the skilled artisan, Applicants contend that the novelty of the method of the invention lies in the unique combination of those steps and techniques coupled with the never-before-described method of introducing a LTVEC directly into eukaryotic cells to modify a chromosomal locus, and the use of quantitative MOA assays to identify eukaryotic cells which have been appropriately modified. This novel combination represents a significant improvement over previous technologies for creating organisms possessing modifications of endogenous genes or chromosomal loci.

EXAMPLES

Example 1

Engineering Mouse ES Cells Bearing a Deletion of the OCR10 Gene.

a. Selection of a Large Genomic DNA Clone Containing mOCR10.

A Bacterial Artificial Chromosome (BAC) clone carrying a large genomic DNA fragment that contained the coding sequence of the mouse OCR10 (mOCR10) gene was obtained by screening an arrayed mouse genomic DNA BAC library (Incyte Genomics) using PCR. The primers employed to screen this library were derived from the mOCR10 gene cDNA sequence.

Two primer pairs where used:
(a) OCR10.RAA (5'-AGCTACCAGCTGCAGAT-GCGGGCAG-3')(SEQ ID NO: 1) and OCR10.PVIrc (5'-CTCCCCAGCCTGGGTCTGAAAGATGACG-3')(SEQ ID NO: 2) which amplifies a 102 bp DNA; and
(b) OCR10.TDY (5'-GACCTCACTTGCTACACTGAC-TAC-3')(SEQ ID NO: 3) and OCR10.QETrc (5'-ACT-TGTGTAGGCTGCAGAAGGTCTCTTG-3')(SEQ ID NO: 4) which amplifies a 1500 bp DNA.

Figure 2:
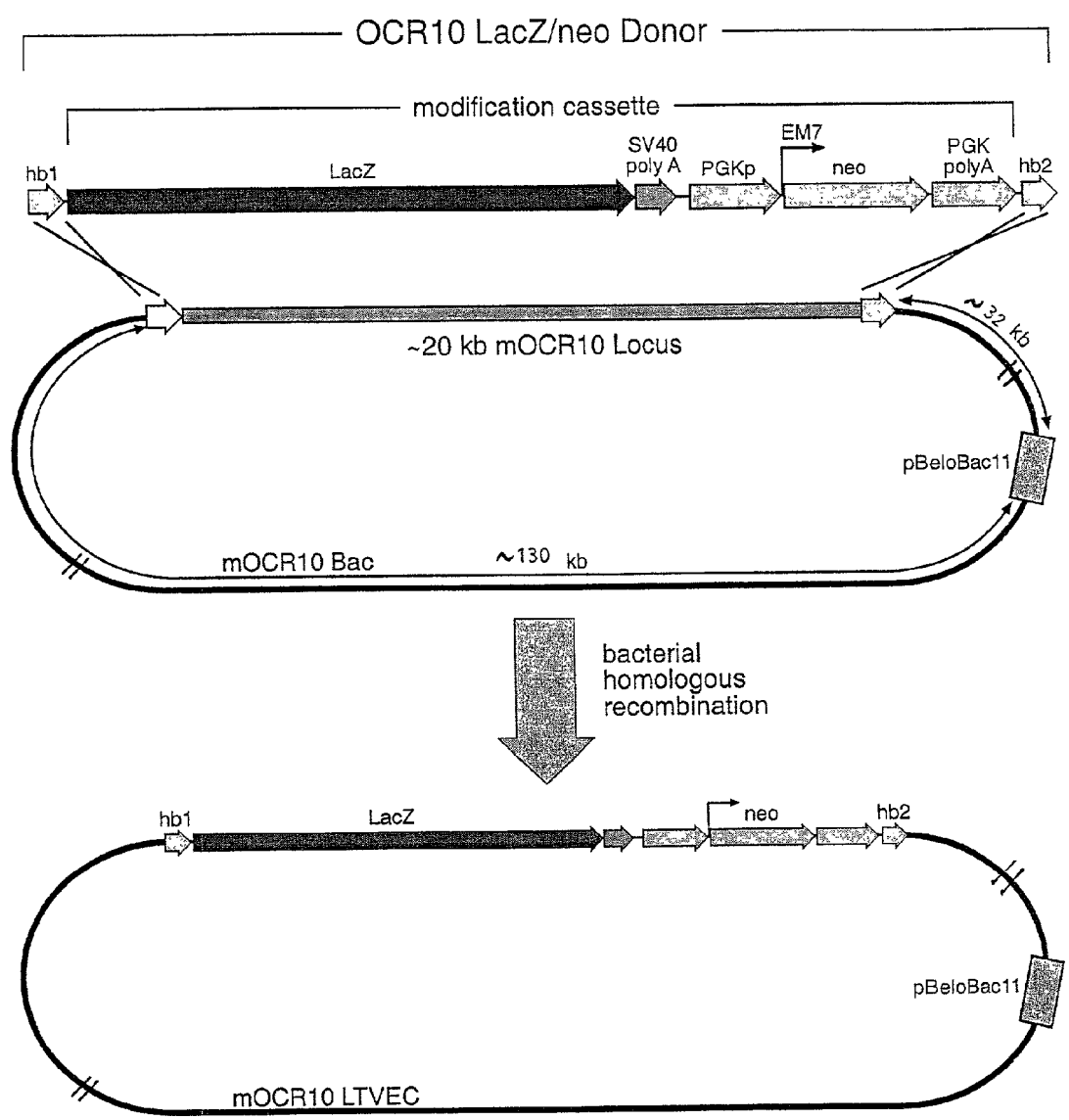
FIG. 2: Schematic diagram of donor fragment and LTVEC for mouse OCR10.
(hb1=homology box 1; lacZ=β-galactosidase ORF; SV40 polyA=a DNA fragment derived from Simian Virus 40, containing a polyadenylation site and signal; PGKp=mouse phosphoglycerate kinase (PGK) promoter; EM7=a bacterial promoter; neo=neomycin phosphotransferase; PGK polyA=3' untranslated region derived from the PGK gene and containing a polyadenylation site and signal; hb2=homology box 2)

This mOCR10 BAC contained approximately 180 kb of genomic DNA including the complete mOCR10 coding sequence. This BAC clone was used to generate an LTVEC which was subsequently used to delete a portion of the coding region of mOCR10 while simultaneously introducing a reporter gene whose initiation codon precisely replaced the initiation codon of OCR10, as well as insertion of a selectable marker gene useful for selection both in *E. coli* and mammalian cells following the reporter gene (FIG. 2). The reporter gene (in this non-limiting example LacZ, the sequence of which is readily available to the skilled artisan), encodes the *E. coli* β-galactosidase enzyme. Because of the position of insertion of LacZ (its initiating codon is at the same position as the initiation codon of mOCR10) the expression of lacZ should mimic that of mOCR10, as has been observed in other examples where similar replacements with LacZ were performed using previous technologies (see "Gene trap strategies in ES cells", by W Wurst and A. Gossler, in Joyner, The Practical Approach Series, 293, 1999) The LacZ gene allows for a simple and standard enzymatic assay to be performed that can reveal its expression patterns in situ, thus providing a surrogate assay that reflects the normal expression patterns of the replaced gene(s) or chromosomal locus(loci).

b. Construction of Donor Fragment and Generation of LTVEC.

The modification cassette used in the construction of the mOCR10 LTVEC is the lacZ-SV40 polyA-PGKp-EM7-neo-PGK polyA cassette wherein lacZ is a marker gene as described above, SV40 polyA is a fragment derived from Simian Virus 40 (Subramanian, et al., Prog Nucleic Acid Res Mol Biol, 19:157–64, 1976; Thimmappaya, et al., J Biol Chem, 253:1613–8, 1978; Dhar, et al., Proc Natl Acad Sci USA, 71:371–5, 1974; Reddy, et al., Science, 200:494–502, 1978) and containing a polyadenylation site and signal (Subramanian, et al., Prog Nucleic Acid Res Mol Biol, 19:157–64, 1976; Thimmappaya, et al., J Biol Chem, 253: 1613–8, 1978; Dhar, et al., Proc Natl Acad Sci USA, 71:371–5, 1974; Reddy, et al., Science, 200:494–502, 1978), PGKp is the mouse phosphoglycerate kinase (PGK) promoter (Adra, et al., Gene, 60:65–74, 1987) (which has been used extensively to drive expression of drug resistance genes in mammalian cells), EM7 is a strong bacterial promoter that has the advantage of allowing for positive selection in bacteria of the completed LTVEC construct by driving expression of the neomycin phosphotransferase (neo) gene, neo is a selectable marker that confers Kanamycin resistance in prokaryotic cells and G418 resistance in eukaryotic cells (Beck, et al., Gene, 19:327–36, 1982), and PGK polyA is a 3' untranslated region derived from the PGK gene and containing a polyadenylation site and signal (Boer, et al., Biochem Genet, 28:299–308, 1990).

To construct the mOCR10 LTVEC, first a donor fragment was generated consisting of a mOCR10 homology box 1 (hb1) attached upstream from the LacZ gene in the modification cassette and a mOCR10 homology box 2 (hb2) attached downstream of the neo-PGK polyA sequence in the modification cassette (FIG. 2), using standard recombinant genetic engineering technology. Homology box 1 (hb1) consists of 211 bp of untranslated sequence immediately upstream of the initiating methionine of the mOCR10 open reading frame (mOCR10 ORF) (FIG. 3A–3D). Homology box 2 (hb2) consists of last 216 bp of the mOCR10 ORF, ending at the stop codon (FIG. 3A–3D).

Subsequently, using bacterial homologous recombination (Zhang, et al., Nat Genet, 20:123–8, 1998; Angrand, et al., Nucleic Acids Res, 27:e116, 1999; Muyrers, et al., Nucleic Acids Res, 27:1555–7, 1999; Narayanan, et al., Gene Ther, 6:442–7, 1999; Yu, et al., Proc Natl Acad Sci USA, 97:5978–83, 2000), this donor fragment was used to precisely replace the mOCR10 coding region (from initiation methionine to stop codon) with the insertion cassette, resulting in construction of the mOCR10 LTVEC (FIG. 2). Thus, in this mOCR10 LTVEC, the mOCR10 coding sequence was replaced by the insertion cassette creating an approximately 20 kb deletion in the mOCR10 locus while leaving approximately 130 kb of upstream homology (upstream homology arm) and 32 kb of downstream homology (downstream homology arm).

It is important to note that LTVECs can be more rapidly and conveniently generated from available BAC libraries than targeting vectors made using previous technologies because only a single bacterial homologous recombination step is required and the only sequence information required is that needed to generate the homology boxes. In contrast, previous approaches for generating targeting vectors using bacterial homologous recombination require that large targeting vectors be "trimmed" prior to their introduction in ES cells (Hill et al., Genomics, 64:111–3, 2000). This trimming is necessary because of the need to generate homology arms short enough to accommodate the screening methods utilized by previous approaches. One major disadvantage of the method of Hill et al. is that two additional homologous recombination steps are required simply for trimming (one to trim the region upstream of the modified locus and one to trim the region downstream of the modified locus). To do this, substantially more sequence information is needed, including sequence information spanning the sites of trimming.

In addition, another obvious advantage, illustrated by the above example, is that a very large deletion spanning the mOCR10 gene (approximately 20 kb) can be easily generated in a single step. In contrast, using previous technologies, to accomplish the same task may require several steps and may involve marking the regions upstream and downstream of the coding sequences with loxP sites in order to use the Cre recombinase to remove the sequence flanked by these sites after introduction of the modified locus in eukaryotic cells. This may be unattainable in one step, and thus may require the construction of two targeting vectors using different selection markers and two sequential targeting events in ES cells, one to introduce the loxP site at the region upstream of the coding sequence and another to introduce the loxP site at the region downstream of the coding sequence. It should be further noted that the creation of large deletions often occurs with low efficiency using the previous targeting technologies in eukaryotic cells, because the frequency of achieving homologous recombination may be low when using targeting vectors containing large deletion flanked by relatively short homology arms. The high efficiency obtained using the method of the invention (see below) is due to the very long homology arms present in the LTVEC that increase the rate of homologous recombination in eukaryotic cells.

c. Verification, Preparation, and Introduction of mOCR10 LTVEC DNA into ES Cells.

The sequence surrounding the junction of the insertion cassette and the homology sequence was verified by DNA sequencing. The size of the mOCR10 LTVEC was verified by restriction analysis followed by pulsed field gel electrophoresis (PFGE) (Cantor, et al., Annu Rev Biophys Biophys Chem, 17:287–304,1988; Schwartz and Cantor, Cell, 37:67–75,1984). A standard large-scale plasmid preparation of the mOCR10 LTVEC was done, the plasmid DNA was digested with the restriction enzyme NotI, which cuts in the vector backbone of the mOCR10 LTVEC, to generate linear DNA. Subsequently the linearized DNA was introduced into mouse ES cells by electroporation (Robertson, Practical Approach Series, 254, 1987; Joyner, The Practical Approach Series, 293, 1999; Sambrook, et al., Sambrook, J., E. F. Fritsch and T. Maniatis. Molecular Cloning: A Laboratory Manual, Second Edition, Vols 1, 2, and 3, 1989). ES cells successfully transfected with the mOCR10 LTVEC were selected for in G418-containing media using standard selection methods (Robertson, Practical Approach Series, 254, 1987; Joyner, The Practical Approach Series, 293, 1999).

d. Identification of Targeted ES Cells Clones using a Quantitative Modification of Allele (MOA) Assay.

To identify ES cells in which one of the two endogenous mOCR 10 genes had been replaced by the modification cassette sequence, DNA from individual ES cell clones was analyzed by quantitative PCR using standard TaqMan® methodology as described (Applied Biosystems, TaqMan® Universal PCR Master Mix, catalog number P/N 4304437. The primers and TaqMan® probes used are as described in FIG. 3A–3D. A total of 69 independent ES cells clones where screened and 3 were identified as positive, i.e. as clones in which one of the endogenous mOCR 10 coding sequence had been replaced by the modification cassette described above.

Several advantages of the MOA approach are apparent:
(i) It does not require the use of a probe outside the locus being modified, thus obviating the need to know the sequence flanking the modified locus.
(ii) It requires very little time to perform compared to conventional Southern blot methodology which has been the previous method of choice (Robertson, Practical Approach Series, 254, 1987, Joyner, The Practical Approach Series, 293, 1999), thus reducing the time for identifying correctly modified cells from the typical several days to just a few hours.

This is a significant improvement in the way screening has been performed in the past and makes it a much less labor-intensive and more cost-effective approach to screening for homologous recombination events in eukaryotic cells.

Yet another advantage of the method of the invention is that it is also superior to previous technologies because of its ability to target difficult loci. Using previous technologies, it has been shown that for certain loci the frequency of successful targeting may by as low as 1 in 2000 integration events, perhaps even lower. Using the method of the invention, Applicants have demonstrated that such difficult loci can be targeted much more efficiently using LTVECs that contain long homology arms (i.e. greater than those allowed by previous technologies). As the non-limiting example described above demonstrates, the Applicants have targeted the OCR10 locus, a locus that has previously proven recalcitrant to targeting using conventional technology. Using the method of the invention, Applicants have shown that they have obtained successful targeting in 3 out of 69 ES cells clones in which the mOCR10 LTVEC (containing more than 160 kb of homology arms, and introducing a 20 kb deletion) had integrated, whereas using previous technology for ES cell targeting (Joyner, The Practical Approach Series, 293, 1999) using a plasmid-based vector with homology arms shorter than 10–20 kb while also introducing a deletion of less than 15 kb, no targeted events were identified among more than 600 integrants of the vector. These data clearly demonstrate the superiority of the method of the invention over previous technologies.

Example 2

Increased Targeting Frequency and Abrogation of the Need to Use Isogenic DNA when LTVECs are Used as the Targeting Vectors.

As noted above, the increased targeting frequency obtained using long homology arms should diminish the benefit, if any, derived from using genomic DNA in constructing LTVECs that is isogenic with (i.e. identical in sequence to) the DNA of the eukaryotic cell being targeted. To test this hypothesis, Applicants have constructed numerous LTVECs using genomic DNA derived from the same mouse substrain as the eukaryotic cell to be targeted (presumably isogenic), and numerous other LTVECs using genomic DNA derived from mouse substrains differing from that of the eukaryotic cell to be targeted (presumably non-isogenic). The two sets of LTVECs exhibited similar targeting frequencies, ranging from 1–13% (Table 1), indicating that the rate of successful targeting using LTVECs does not depend on isogenicity.

TABLE 1

SUMMARY OF GENE TARGETING USING BAC CLONE VECTORS

| | | | | Approx. (Kb) | | | | | |
|---|---|---|---|---|---|---|---|---|---|
| Target Gene | Description | DNA Origin | ES-cell | LTVEC size | Arm 1 | Arm 2 | Del | + clones | % targeting |
| NON-ISOGENIC | | | | | | | | | |
| OGH | LacZ-ATG fusion | SvJ | CJ7 | 147 | 50 | 90 | 5 | 4 | 4 |
| OCR10(A) | LacZ-ATG fusion | SvJ | CJ7 | 150 | 135 | 8 | 20 | 1 | 1.4 |
| OCR10(B) | LacZ-ATG fusion | SvJ | CJ7 | 169 | 130 | 32 | 20 | 3 | 4.3 |
| MA61 | LacZ-ATG fusion | SvJ | CJ7 | 95 | N/D | N/D | 30 | 3 | 4.6 |
| MA16 | LacZ-ATG fusion | SvJ | CJ7 | 120 | N/D | N/D | 8 | 8 | 13 |

TABLE 1-continued

SUMMARY OF GENE TARGETING USING BAC CLONE VECTORS

| | | | | Approx. (Kb) | | | | | |
|---|---|---|---|---|---|---|---|---|---|
| Target Gene | Description | DNA Origin | ES-cell | LTVEC size | Arm 1 | Arm 2 | Del | + clones | % targeting |
| ISOGENIC | | | | | | | | | |
| ROR1 | Intracell-LacZ fusion | CJ7 | CJ7 | 55 | 14 | 14 | 20 | 5 | 5 |
| ROR1 | Intracell-3xmyc fusion | CJ7 | CJ7 | 55 | 14 | 14 | 20 | 2 | 2 |
| ROR2 | Brachydactyly mutation and Myc tag | CJ7 | CJ7 | 45 | 11 | 24 | 0.5 | 2 | 2 |

In summary, the approach of creating LTVECs and directly using them as targeting vectors combined with MOA screening for homologous recombination events in ES cells creates a novel method for engineering genetically modified loci that is rapid, inexpensive and represents a significant improvement over the tedious, time-consuming methods previously in use. It thus opens the possibility of a rapid large scale in vivo functional genomics analysis of essentially any and all genes in an organism's genome in a fraction of the time and cost necessitated by previous methodologies.

Example 3

Use of LTVEC's to Produce Chimeric and Human Antibodies a. Introduction

Antibodies are composed of two chains, the light and heavy chains, each of which are composed of two domains, the variable and constant domains. The variable region of the antibody protein is the N-terminal portion of the antibody, which binds the antigen. The heavy chain variable domain is encoded by the DNA of the heavy chain variable gene locus, which is composed of the variable (V), the diversity (D), and the joining (J) gene segments. The light chain variable domains are encoded by the DNA of the light chain variable gene loci, kappa and lambda, which are composed of the variable (V) and joining (J) gene segments.

The rearrangement of variable region (VDJ/VJ) genes during the initial development of B cells is the primary mechanism whereby the immune system produces antibodies capable of recognizing the huge number of antigens that it may encounter. Essentially, through DNA rearrangements during B cell development, a huge repertoire of variable (VDJ/VJ) region sequences are assembled which are subsequently joined to a constant (C) region to produce complete heavy and light chains which assemble to form an antibody. After functional antibodies have been assembled, somatic hypermutation which occurs in the secondary lymphoid organs, introduces further diversity which enables the organism to select and optimize the affinity of the antibody.

The production of antibodies to various antigens in non-human species initially provided great promise for the large scale production of antibodies that could be used as human therapeutics. Species differences, however, leads to the production of antibodies by humans which inactivate the foreign antibodies and cause allergic reactions. Attempts were subsequently made to "humanize" the antibodies, thus making them less likely to be recognized as foreign in humans. Initially, this process involved combining the antigen binding portions of antibodies derived from mice with the constant region of human antibodies, thereby creating recombinant antibodies that were less immunogenic in humans. A second approach which was developed was phage display, whereby human V regions are cloned into a phage display library and regions with the appropriate binding characteristics are joined to human constant regions to create human antibodies. This technology is limited, however, by the lack of antibody development and affinity maturation which naturally occurs in B cells.

More recently, endogenous genes have been knocked out of mice, and the genes replaced with their human counterparts to produce entirely human antibodies. Unfortunately, the use of these constructs has highlighted the importance of an endogenous constant region in the development and optimization of antibodies in B cells. Mice producing fully human antibodies have reduced immune responses. This may because human antibodies produced by transgenic mice with entirely human constructs have reduced affinity as compared to their mouse counterparts. Reduced affinity could effect B-cell maturation and survival. Accordingly, the much acclaimed methods of producing humanized antibodies in mice and other organisms, wherein endogenous variable and constant regions of the mice are knocked out and replaced with their human counterparts, has not resulted in optimal antibodies.

The use of chimeric antibodies, which utilize human variable regions (VDJ/VJ) with mouse constant regions through B cell maturation, followed by subsequent engineering of the antibodies to replace the mouse constant regions with their human counterparts, has been suggested (U.S. Pat. No. 5,770,429 issued Jun. 23, 1998). However, the only methodology that has existed to date for making such chimeras has been trans-switching, wherein the formation of the chimeras is only a rare event which occurs only in heavy chains. Heretofore, there has been no mechanism to produce, in transgenic animals, large scale replacement of the entire variable gene encoding segments with human genes, thereby producing chimeras in both the heavy and light chains. Utilizing applicants technology, as disclosed herein, chimeric antibodies are generated which can then be altered, through standard technology, to create high affinity human antibodies.

b. Brief Description

A transgenic mouse is created that produces hybrid antibodies containing human variable regions (VDJ/VJ) and mouse constant regions. This is accomplished by a direct, in situ replacement of the mouse variable region (VDJ/VJ) genes with their human counterparts. The resultant hybrid immunoglobulin loci will undergo the natural process of rearrangements during B-cell development to produce the hybrid antibodies.

Subsequently, fully-human antibodies are made by replacing the mouse constant regions with the desired human counterparts. This approach will give rise to therapeutic antibodies much more efficiently than previous methods, e.g. the "humanization" of mouse monoclonal antibodies or the generation of fully human antibodies in HuMAb mice. Further, this method will succeed in producing therapeutic antibodies for many antigens for which previous methods have failed. This mouse will create antibodies that are human (VDJ/VJ)-mouse constant region, which will have the following benefits over the previously available HuMAb mice that produce totally human antibodies. Antibodies generated by the new mouse will retain murine Fc regions which will interact more efficiently with the other components of the mouse B cell receptor complex, including the signaling components required for appropriate B cell differentiation (such as Iga and Igb). Additionally, the murine Fc regions will be more specific than human Fc regions in their interactions with Fc receptors on mouse cells, complement molecules, etc. These interactions are important for a strong and specific immune response, for the proliferation and maturation of B cells, and for the affinity maturation of antibodies.

Because there is a direct substitution of the human V-D-J/V-J regions for the equivalent regions of the mouse loci all of the sequences necessary for proper transcription, recombination, and/or class switching will remain intact. For example, the murine immunoglobulin heavy chain intronic enhancer, Em, has been shown to be critical for V-D-J recombination as well as heavy chain gene expression during the early stages of B cell development [Ronai, D. Berru, M., and Shulman, M. J. Mol Cell Biol 19:7031–7040 (1999)], whereas the immunoglobulin heavy chain 3' enhancer region appears to be critical for class switching [Pan, Q., Petit-Frere, C., Stavnezer, J., and Hammarstrom, L. Eur J Immunol 30:1019–1029 (2000)] as well as heavy chain gene expression at later stages of B cell differentiation [Ong, J., Stevens, S., Roeder, R. G., and Eckhardt, L. A. J Immunol 160:4896–4903 (1998)]. Given these various, yet crucial, functions of the transcriptional control elements, it is desirable to maintain these sequences intact.

The required recombination events which occur at the immunoglobulin loci during the normal course of B cell differentiation may increase the frequency of aberrant, non-productive immunoglobulin rearrangements when these loci are inserted at improper chromosomal locations, or in multiple copies, as in currently available mice. With reductions in productive immunoglobulin rearrangement and, therefore, appropriate signaling at specific steps of B cell development the aberrant cells are eliminated. Reductions of B cell numbers at early stages of development significantly decreases the final overall B cell population and greatly limits the immune responses of the mice. Since there will be only one, chimeric, heavy or light chain locus (as opposed to mutated immunoglobulin loci and with human transgenic loci integrated at distinct chromosomal locations for heavy and light chains in the currently available mice) there should be no trans-splicing or trans-rearrangements of the loci which could result in non-productive rearrangements or therapeutically irrelevant chimeric antibodies (Willers, J., Kolb, C. and Weiler, E. Immunobiology 200:150–164 (2000); Fujieda, S., Lin, Y. Q., Saxon, A., and Zhang, K. J Immunol 157:3450–3459 (1996)).

The substitutions of the human V-D-J or V-J regions into the genuine murine chromosomal immunoglobulin loci should be substantially more stable, with increased transmission rates to progeny and decreased mosaicism of B cell genotypes compared with the currently available mice (Tomizuka, K., Shinohara, T., Yoshida, H., Uejima, H., Ohguma, A., Tanaka, S., Sato, K., Oshimura, M., and Ishida, I. Proc Natl Acad Sci (USA) 97:722–727 (2000)). Furthermore, introduction of the human variable regions (VDJ/VJ) at the genuine murine loci in vivo will maintain the appropriate global regulation of chromatin accessibility previously shown to be important for appropriately timed recombination events (Haines, B. B., and Brodeur, P. H. Eur J Immunol 28:4228–4235 (1998)).

Approximately ⅓ of human antibodies contain lambda light chains, as compared to mice in which only ¹⁄₂₀ of murine antibodies contain lambda light chains. Therefore, replacing murine lambda light chain V-J sequences with lambda light chain V-J sequences derived from the human locus will serve to increase the repertoire of antibodies as well as more closely match the genuine human immune response, thus increasing the likelihood of obtaining therapeutically useful antibodies.

An additional benefit of integrating the human sequences into the genuine murine immunoglobulin loci is that no novel integration sites are introduced which might give rise to mutagenic disruptions at the insertion site and preclude the isolation of viable homozygous mice. This will greatly simplify the production and maintenance of a breeding mouse colony.

The following provides a novel method for producing antibodies with all of the above advantages. One skilled in the art will recognize that the general method described herein can be modified to produce equivalent results.

c. Materials and Methods:

Precise replacement of the mouse heavy chain locus variable region (VDJ) with its human counterpart is exemplified using a combination of homologous and site-specific recombination in the following example, which utilizes a two step process. One skilled in the art will recognize that replacement of the mouse locus with the homologous or orthologous human locus may be accomplished in one or more steps. Accordingly, the invention contemplates replacement of the murine locus, in whole or in part, with each integration via homologous recombination.

Large insert (BAC) clones spanning the entire VDJ region of the human heavy chain locus are isolated (FIG. 4A). The sequence of this entire region is available in the following GenBank files (AB019437, AB019438, AB019439, AB019440, AB019441, X97051 and X54713). In this example, large insert (BAC) clones are isolated from the ends of the mouse VDJ region as a source of homology arms (FIG. 4B) which are used to direct integration via homologous recombination of the human VDJ sequences in a two step process.

In the first step, LTVEC1 (FIG. 4D) is constructed by bacterial homologous recombination in $E.\ coli$. LTVEC1 contains, in order: a large mouse homology arm derived from the region upstream from the mouse DJ region but whose absolute endpoints are not important; a cassette encoding a selectable marker functional in ES cells (PGK-neomycinR in this example); a loxP site; a large human insert spanning from several V gene segments through the entire DJ region; and a mouse homology arm containing the region immediately adjacent to, but not including, the mouse J segments. The 5' end of the downstream arm and the placement of the loxP sites define the 3' end of the region to be replaced in the locus. Mouse ES cells will be transformed by standard techniques, for example, electroporation, with linearized LTVEC1. Because direct introduction of LTVEC1 results in a modification of the endogenous variable gene locus, neomycin resistant colonies can be screened for correct targeting using a MOA assay. These targeted ES cells can give rise to mice that produce antibodies with hybrid heavy chains. However, it will be preferable to proceed with subsequent steps that will eliminate the remainder of the mouse variable segments.

In the second step, LTVEC2 (FIG. 4C) is constructed by bacterial homologous recombination in E. coli. LTVEC2 contains, in order: a large mouse homology arm containing the region adjacent to the most distal mouse V gene segment, but not containing any mouse V gene segments; a large insert containing a large number of distal human V gene segments; a mutant loxP site called lox511 [Hoess, R. H., Wierzbicki, A. and Abremski, K. Nucleic Acids Res. 14:2287–2300 (1986)] in the orientation opposite to that of the wild type loxP sites in LTVEC2 and LTVEC1 (this site will not recombine with wild type loxP sites but will readily recombine with other lox511 sites); a wild type loxP site; a second selectable marker (PGK-hygromycinR in this example); and a mouse homology arm derived from the V region, but whose absolute endpoints are not important. The 3' end of the upstream homology arm and the placement of the loxP sites define the 5' end of the region to be replaced in the locus. Mouse ES cells that were correctly targeted with LTVEC1 will then be transformed by standard techniques with linearized LTVEC2, and hygromycin resistant colonies will be screened for correct targeting using a MOA assay for modifications in the endogenous variable gene locus. Correctly targeted ES cells resulting from this transformation will hereafter be referred to as "double targeted ES cells".

Subsequent transient expression of CRE recombinase in the double targeted ES cells will result in deletion of the remainder of the mouse V region. Alternatively, the double targeted ES cells can be injected into host blastocysts for the production of chimeric mice. Breeding of the resultant chimeric mice with mice expressing CRE recombinase early in development will result in deletion of the remainder of the mouse V region in the progeny F1. This later alternative increases the likelihood that the hybrid heavy chain locus will be passed through the germline because it involves culturing the ES cells for fewer generations.

The inclusion of lox511 in LTVEC2 will allow for the insertion of additional human V gene segments into the hybrid locus. One approach would be to use bacterial homologous recombination to flank a large genomic DNA clone containing many additional human V gene segments with lox511 and loxP sites. Co-transformation of such a modified large genomic DNA clone into double targeted ES cells with a plasmid that transiently expresses CRE recombinase will result in the introduction of the additional V gene segments by cassette exchange (Bethke, B. and Sauer, B. Nucleic Acids Res. 25:2828–2834 (1997)).

A second approach to the incorporation of additional V gene segments is to independently target a large genomic DNA clone containing many additional human V gene segments into the mouse locus using, for instance, the same mouse homology arms included in LTVEC2. In this case, the additional human V gene segments would be flanked by lox511 and loxP sites, and the targeted ES cells would be used to create a mouse. The mice derived from double targeted ES cells and the mice derived from the ES cells containing the additional V gene segments would be bred with a third mouse that directs expression of CRE recombinase during meiosis. The close proximity of the two recombinant loci during meiotic pairing would result in a high frequency of CRE induced inter-chromosomal recombination as has been seen in other systems (Hérault, Y., Rassoulzadegan, M., Cuzin, F. and Duboule, D. Nature Genetics 20: 381–384 (1998)).

Another approach is similar to that outlined above but, rather than introducing the loxP and lox511 sites with human LTVECs 1 and 2, they are introduced on mouse LTVECs and then CRE is used to specifically target in the human loci by cassette exchange via flanking loxP and lox511 sites. The methodology outlined below demonstrates how the LTVEC technology may be used to place flanking site specific recombination sites at the ends of any endogenous gene of interest in any non-human animal.

Mouse LTVEC 1 contains a cassette inserted by bacterial recombination downstream of, and adjacent to, the J region. This cassette contains a loxP site and a bacterial/mammalian selectable marker, such as hygromycin resistance. LTVEC1 contains, in order: a large homology arm derived from the region upstream from the mouse DJ region (but within the variable gene locus), but whose absolute endpoints are not important; a cassette encoding a selectable marker functional in ES cells (PGK-hygromycinR in this example); a loxP site; and a homology arm containing the region immediately adjacent to, but not including, the mouse J segments. The 5' end of the downstream homology arm and the placement of the loxP sites define the 3' end of the region to be replaced in the locus. Modification of the 3' end of the endogenous variable gene at the site of cassette insertion allows for the detection of correctly inserted LTVEC1 in the ES cells by an MOA assay. Drug resistance markers are flanked by FRT sites. The introduction of FRT sites allows the removal of any remaining drug resistance markers by FLPe either in ES cells or by crossing the resulting mice to a mice that expresses FLPe in cells that have germ-line potential.

LTVEC2 is constructed by bacterial recombination to insert a cassette upstream of the most distal V region of the loci. This cassette contains a lox511 site and a bacteria/mammalian selectable marker, such as neomycin resistance. LTVEC2 contains, in order: a large homology arm containing the region adjacent to the most distal mouse V gene segment, but not containing any mouse V gene segments; a lox511 site in the orientation opposite to that of the wild type loxP sites in LTVEC2 and LTVEC1; a wild type loxP site; a second selectable marker (PGK-neomycinR in this example); and a mouse homology arm derived from the V region (and therefore within the variable gene locus), but whose absolute endpoints are not important. The 3' end of the upstream homology arm and the placement of the loxP sites define the 5' end of the region to be replaced in the locus. Modification of the 5' end of the endogenous variable gene at the site of cassette insertion allows for the detection of correctly inserted LTVEC2 in the ES cells by an MOA assay. These LTVECs are introduced together or sequentially into ES cells using standard techniques and screened for correct targeting using an MOA assay.

A human BAC containing the VDJ/VJ region, in part or in whole, is modified by bacterial recombination to insert cassettes that flank the human sequences with lox511 and loxP sites. The upstream cassette is inserted just upstream of the region that will replace the mouse variable region, and contains, in order, a lox511 site followed by a bacteria/mammalian selectable marker, such as puromycin resistance. The downstream cassette is inserted downstream of, and adjacent to, the J region and contains, in order, a loxP site followed by a selectable marker for bacteria, such as spectinomycin resistance.

Several methods may be used to insert a larger piece of the human variable region than occurs on a single BAC isolated from a library. A few of these are described below.

The loxP and lox511 sites can be inserted separately, by bacterial recombination, onto overlapping BACs, which recombine with each other when transformed into ES cells. In this case, the upstream BAC has one cassette, recombined just upstream of the region that will replace the mouse variable region, that has a lox511 site followed by a bacterial/mammalian selectable marker, such as neomycin resistance. The downstream BAC has one cassette, recombined just downstream of, and adjacent to, the J region, that contains a bacterial/mammalian selectable marker, such as puromycin resistance followed by a loxP site. If these two BACs are not overlapping, additional BACs that link the upstream and downstream BACs by overlapping homology are incorporated into the scheme. These are modified by bacterial recombination to contain bacterial/mammalian selectable markers, such as puromycin resistance, and the upstream and downstream BACs are modified to contain loxP and lox511 cassettes that carrying neomycin and hygromycin resistance markers.

The human BAC(s) are co-transformed with CRE recombinase into the ES cell line containing the variable-region-flanking lox511 and loxP recombination sites. If overlapping BACs are used, homologous recombination occurs between them to create a larger DNA fragment, and the flanking loxP and lox511 sites target this large fragment into the mouse locus. Cells are selected for puromycin resistance and screened for the replacement of the mouse variable region. Alternatively, the mouse sequences can first be deleted via the two loxP sites and then the human sequences can be introduced via the remaining lox511 and loxP sites.

A fourth BAC can be inserted if LTVEC1 also contains a third site specific recombination site, e.g. lox2272 (Anal Biochem 2001 Mar. 15;290(2):260–71) just downstream of the bacterial/mammalian resistance gene, such as puromycin resistance, creating a LTVEC with, in order, the puromycin resistance gene, a loxP site, and a lox2272 site, followed by the human sequences. After this BAC is integrated into the mouse immunoglobulin locus, the lox511/lox2272 sites can serve as a recipient in a second round of cassette exchange, wherein the puromycin resistance gene is replaced by an additional upstream portion of the human immunoglobulin locus variable region and a different bacterial/mammalian resistance gene flanked by lox511 and lox2272 sites.

Another method for inserting a larger stretch of the human variable region is to combine sequences from multiple BACs in vitro using rare restriction endonuclease cleavage sites. This is accomplished by using bacterial homologous recombination to insert a loxP site and spectinomycin resistance gene just downstream of the last J of the most downstream BAC and inserting a second bacterial selectable marker and a rare I-Ceu1 site at the upstream end of the human sequences of the downstream BAC. A lox511 site and a bacterial/mammalian selectable marker, e.g. puromycin resistance, is inserted at the upstream end of a second BAC containing a region of the human variable region upstream from the sequences in the first BAC. An I-Ceu1 site is inserted at the downstream end of the second BAC. After digestion of both BACs with I-Ceu1 and Not1, which is unique in the vector portion of both modified BACs, the two BACs are ligated and a recombinant is selected in bacteria for puromycin and spectinomycin resistance. The resultant larger BAC contains, in order, a lox511 site, upstream human sequences, a I-Ceu1 site, downstream human sequences, a loxP site and a spectinomycin resistance gene. The region between the lox511 site and the loxP site are inserted into the mouse immunoglobulin locus by cassette exchange and puromycin selection as described above.

A third method for inserting a larger stretch of the human variable region is to combine sequences from multiple BACs as described above, but using bacterial homologous recombination instead of restriction digestion/ligation. The same selection for recombinant BACs is applied in bacteria, except only one of the two BACs would be digested, its ends after digestion would be designed to be homologous to the other "recipient" BAC, and the recipient BAC would be in bacterial strain modified to be permissive for bacterial homologous recombination.

The final steps in creating the human variable/mouse constant monoclonal antibody producing-mouse will be performing the equivalent variable region substitutions on the lambda and kappa light chain loci and breeding all three hybrid loci to homozygocity together in the same mouse. The resultant transgenic mouse will have a genome comprising entirely human heavy and light chain variable gene loci operably linked to entirely endogenous mouse constant region such that the mouse produces a serum containing an antibody comprising a human variable region and a mouse constant region in response to antigenic stimulation. Such a mouse may then be used as a source of DNA encoding the variable regions of human antibodies. Using standard recombinant technology, DNA encoding the variable regions of the heavy and light chains of the antibody is operably linked to DNA encoding the human heavy and light chain constant regions in cells, such as a CHO cells, which are capable of expressing active antibodies. The cells are grown under the appropriate conditions to express the fully human antibodies, which are then recovered. Variable region encoding sequences may be isolated, for example, by PCR amplification or cDNA cloning. In a preferred embodiment, hybridomas made from transgenic mice comprising some or all of the human variable region immunoglobulin loci (Kohler and Milstein, Eur. J. Immunol., 6:511–519 (1976) are used as a source of DNA encoding the human variable regions.

In summary, the approach of creating LTVECs and directly using them as targeting vectors combined with MOA screening for homologous recombination events in ES cells creates a novel method for engineering genetically modified loci that is rapid, inexpensive and represents a significant improvement over the tedious, time-consuming methods previously in use. It thus opens the possibility of a rapid large scale in vivo functional genomics analysis of essentially any and all genes in an organism's genome in a fraction of the time and cost necessitated by previous methodologies.

Although the foregoing invention has been described in some detail by way of illustration and examples, it will be readily apparent to those of ordinary skill in the art that certain changes and modifications may be made to the teachings of the invention without departing from the spirit or scope of the appended claims.

We claim:

1. A method of creating, in an isolated mouse embryonic stem (ES) cell, a genetically modified endogenous gene locus flanked downstream by a site-specific recombination site comprising:
    (a) using bacterial homologous recombination to genetically modify a cloned genomic fragment of an endogenous gene locus to create a large targeting vector for use in eukaryotic cells (LTVEC), said LTVEC comprising a site-specific recombination site, a downstream homology arm containing a region homologous to the 3' end of the endogenous gene locus region and an upstream homology arm within the locus, wherein the homology arms are larger than 20 kb and the site-specific recombination site is selected from one or more of loxP, lox511, and lox2272;
    (b) introducing the LTVEC of (a) into an isolated mouse ES cell; and
    (d) using a quantitative assay with a probe directed to an unmodified allele of the endogenous gene locus to detect reduced copy number of the unmodified allele compared to that of a reference gene in the cell from (b) thereby indicating modification of allele (MOA) in the endogenous gene locus of the cell, wherein the endogenous gene locus is flanked downstream by the site-specific recombination site.

2. A method of creating, in an isolated mouse embryonic stem (ES) cell, a genetically modified endogenous gene locus flanked upstream by a site-specific recombination site comprising:
    (a) using bacterial homologous recombination to genetically modify a cloned genomic fragment of an endogenous gene locus to create a large targeting vector for use in eukaryotic cells (LTVEC), said LTVEC comprising a site-specific recombination site, an upstream homology arm containing a region homologous to the 5' end of the endogenous gene locus region and a downstream homology arm within the locus, wherein the homology arms are larger than 20 kb and the site-specific recombination site is selected from one or more of loxP, lox511, and lox2272;
    (b) introducing the LTVEC of (a) into an isolated mouse ES cell; and
    (c) using a quantitative assay with a probe directed to an unmodified allele of the endogenous gene locus to detect reduced copy number of the unmodified allele compared to that of a reference gene in the cell from (b) thereby indicating modification of allele (MOA) in the endogenous gene locus of the cell, wherein the endogenous gene locus is flanked downstream by the site-specific recombination site.

3. A method of creating, in an isolated mouse embryonic stem (ES) cell, a genetically modified endogenous gene locus flanked by site-specific recombination sites comprising:
    (a) using bacterial homologous recombination to genetically modify a cloned genomic fragment of an endogenous gene locus to create a first large targeting vector for use in eukaryotic cells (LTVEC), said LTVEC comprising a site-specific recombination site, a downstream homology arm containing a region homologous to the 3' end of the endogenous gene locus region and an upstream homology arm within the locus, wherein the homology arms are larger than 20 kb and the site-specific recombination site is selected from one or more of loxP, lox511, and lox2272;
    (b) using bacterial homologous recombination to create a second LTVEC comprising the site-specific recombination site, an upstream homology arm containing a region that flanks the 5' end of the endogenous gene locus region and a downstream homology arm within the locus;
    (c) introducing the first and second LTVECs into an isolated mouse ES cell; and
    (d) using a quantitative assay with a probe directed to an unmodified allele of the endogenous gene locus to detect reduced copy number of the unmodified allele compared to that of a reference gene in the cell from (c) thereby indicating modification of allele (MOA) in the endogenous gene locus of the cell, wherein the site-specific recombination sites are flanking the endogenous gene locus.

4. The method of claim 3, further comprising:
    (e) introducing a recombinase into the cell identified in step (d), wherein the endogenous gene locus flanked by the site-specific recombination sites is deleted.

5. The method of claim 4, further comprising:
    (f) creating a vector containing the site-specific recombination sites flanking a replacing gene locus; and
    (g) introducing the vector of (f) into the cell of (e) such that, through recombination, the replacing gene locus is inserted between the site-specific recombination sites.

6. The method of claim 4, further comprising:
    (f) obtaining a large cloned genomic fragment containing, in whole or in part, a replacing region gene locus;
    (g) using bacterial homologous recombination to genetically modify the cloned fragment of (f) to create a third LTVEC comprising the replacing region gene locus flanked by a downstream homology arm containing a region homologous to the 3' end of the endogenous gene locus region and an upstream homology arm containing a region homologous to the 5' end of the endogenous gene locus region; and
    (h) introducing the third LTVEC of (g) into the cell of (e) to replace the deleted endogenous gene locus.

7. The method of claim 4, wherein the recombinase is CRE.

8. The method of claim 1, 2 or 3, wherein the quantitative assay comprises quantitative PCR, FISH, comparative genomic hybridization, isothermic DNA amplification, or quantitative hybridization to an immobilized probe.

9. A method of creating, in an isolated mouse embryonic stem (ES) cell, a genetically modified endogenous immunoglobulin variable region gene locus flanked downstream by a site-specific recombination site comprising:
    (a) using bacterial homologous recombination to genetically modify a cloned genomic fragment of an endogenous immunoglobulin variable region gene locus to create a large targeting vector for use in eukaryotic cells (LTVEC), said LTVEC comprising a site-specific recombination site, a downstream homology arm containing a region homologous to the 3' end of the endogenous immunoglobulin variable gene locus region and an upstream homology arm within the locus, wherein the homology arms are larger than 20 kb and the site-specific recombination site is selected from one or more of loxP, lox511, and lox2272;
    (b) introducing the LTVEC of (a) into an isolated mouse ES cell; and
    (c) using a quantitative assay with a probe directed to an unmodified allele of the endogenous gene locus to detect reduced copy number of the unmodified allele compared to that of a reference gene in the cell from (b) thereby indicating modification of allele (MOA) in the endogenous immunoglobulin variable region gene locus of the cell, wherein the endogenous immunoglobulin variable region gene locus is flanked downstream by the site-specific recombination site.

10. A method of creating, in an isolated mouse embryonic stem (ES) cell, a genetically modified endogenous immunoglobulin variable region gene locus flanked upstream by a site-specific recombination site comprising:
(a) using bacterial homologous recombination to genetically modify a cloned genomic fragment of an endogenous immunoglobulin variable region gene locus to create a large targeting vector for use in eukaryotic cells (LTVEC), said LTVEC comprising a site-specific recombination site, an upstream homology arm containing a region homologous to the 5' end of the endogenous immunoglobulin variable gene locus region and a downstream homology arm within the locus, wherein the homology arms are larger than 20 kb and the site-specific recombination site is selected from one or more of loxP, lox511, and lox2272;
(b) introducing the LTVEC of (a) into an isolated mouse ES cell; and
(c) using a quantitative assay with a probe directed to an unmodified allele of the endogenous gene locus to detect reduced copy number of the unmodified allele compared to that of a reference gene in the cell from (b) thereby indicating modification of allele (MOA) in the endogenous immunoglobulin gene locus of the cell, wherein the endogenous gene locus is flanked downstream by the site-specific recombination site.

11. A method of creating, in an isolated mouse embryonic stem (ES) cell, a genetically modified endogenous immunoglobulin variable region gene locus flanked site-specific recombination sites comprising:
(a) using bacterial homologous recombination to genetically modify a cloned genomic fragment of an endogenous immunoglobulin variable region gene locus to create a first large targeting vector for use in eukaryotic cells (LTVEC), said LTVEC comprising a site-specific recombination site, a downstream homology arm containing a region homologous to a 3' end of the endogenous immunoglobulin variable gene locus region and an upstream homology arm within the locus, wherein the homology arms are larger than 20 kb and the site-specific recombination site is selected from one or more of loxP, lox511, and lox2272;
(b) using bacterial homologous recombination to genetically modify a cloned genomic fragment of an endogenous immunoglobulin variable region gene locus to create a second LTVEC comprising a site-specific recombination site, an upstream homology arm containing a region that flanks the 5' end of the endogenous immunoglobulin variable region gene locus region and a downstream homology arm within the locus;
(c) introducing the first and second LTVECs into an isolated mouse ES cell; and
(d) using a quantitative assay with a probe directed to an unmodified allele of the endogenous immunoglobulin variable region gene locus to detect reduced copy number of the unmodified allele compared to that of a reference gene in the cell from (c) thereby indicating modification of allele (MOA) in the endogenous gene locus of the cell, wherein the endogenous gene locus is flanked downstream by the site-specific recombination site.

12. The method of claim 11, further comprising:
(e) introducing a recombinase into the cell identified in step (d), wherein the endogenous immunoglobulin variable region gene locus flanked by the site-specific recombination sites is deleted.

13. The method of claim 12, further comprising:
(f) creating a vector containing the site-specific recombination sites flanking a human immunoglobulin variable region gene locus; and (g) introducing the vector of (f) into the cell of (e) such that, through recombination, the human immunoglobulin variable region gene locus, in whole or in part, is inserted between the site-specific recombination sites.

14. The method of claim 11, further comprising:
(f) obtaining a large cloned genomic fragment containing, in whole or in part, a human immunoglobulin variable region gene locus;
(g) using bacterial homologous recombination to genetically modify the cloned fragment of (f) to create a third LTVEC comprising the replacing region gene locus flanked by a downstream homology arm containing a region homologous to the 3' end of the endogenous gene locus region and an upstream homology arm containing a region homologous to the 5' end of the endogenous gene locus region; and
(h) introducing the third LTVEC of (g) into the cell of (e) to replace the deleted endogenous gene locus.

15. A method of replacing, in an isolated mouse embryonic stem (ES) cell, in whole or in part, an endogenous immunoglobulin variable region gene locus with part or all of a human immunoglobulin variable region gene locus comprising:
(a) using bacterial homologous recombination to genetically modify a cloned genomic fragment of an endogenous immunoglobulin variable region gene locus to create a first large targeting vector for use in eukaryotic cells (LTVEC), said LTVEC comprising a site-specific recombination site, a downstream homology arm containing a region immediately adjacent to, but not including, the J segments of the immunoglobulin variable gene locus region and an upstream homology arm within the variable gene locus, wherein the homology arms are larger than 20 kb and the site-specific recombination site is selected from one or more of loxP, lox511, and lox2272;
(b) using bacterial homologous recombination to genetically modify a cloned genomic fragment of an endogenous immunoglobulin variable region gene locus to create a second LTVEC comprising a site-specific recombination site, an upstream homology arm containing a region adjacent to the most distal V gene segment, but not containing any V gene segments of the immunoglobulin variable gene locus region and a downstream homology arm within the variable gene locus, wherein the homology arms are larger than 20 kb;
(c) introducing the first and second LTVECs into an isolated mouse ES cell;
(d) using a quantitative assay with a probe directed to an unmodified allele of the endogenous gene locus to detect reduced copy number of the unmodified allele compared to that of a reference gene in the cell from (c) thereby indicating modification of allele (MOA) in the endogenous variable gene locus of the ES cell, wherein the site-specific recombination sites flank the endogenous variable region gene locus;
(e) creating a vector containing site-specific recombination sequences flanking all or part of a human immunoglobulin variable gene locus; and
(f) introducing the vector of (e) into the cell identified in (d) such that, through recombination, the endogenous immunoglobulin variable region gene locus is replaced, in whole or in part, with all or part of a human immunoglobulin variable gene locus.

* * * * *